United States Patent [19]
Kniss

[11] Patent Number: 5,859,229
[45] Date of Patent: Jan. 12, 1999

[54] ANTISENSE OLIGONUCLEOTIDES TO SUPPRESS EICOSANOID FORMATION

[75] Inventor: Douglas A. Kniss, Hilliard, Ohio

[73] Assignee: The Ohio State University, Columbus, Ohio

[21] Appl. No.: 627,254

[22] Filed: Apr. 3, 1996

Related U.S. Application Data

[63] Continuation of Ser. No. 170,089, Dec. 17, 1993, abandoned.

[51] Int. Cl.$^6$ .......................... C07H 21/00; A61K 31/70; A61K 31/74; A61K 48/00
[52] U.S. Cl. ....................... 536/24.5; 536/23.1; 536/24.3; 536/24.31; 536/24.32; 536/24.33; 435/6; 435/375; 514/44
[58] Field of Search .................................. 536/24.5, 23.1, 536/24.3, 24.31, 24.32, 24.33; 514/44; 435/6, 172.3, 240.2, 325, 354, 366, 375; 935/33, 34, 8

[56] References Cited

U.S. PATENT DOCUMENTS

| 5,112,868 | 5/1992 | Cetenko .................................. 514/618 |
| 5,219,874 | 6/1993 | Faull et al. ............................. 514/365 |
| 5,543,297 | 8/1996 | Cromlish et al. ......................... 435/25 |

FOREIGN PATENT DOCUMENTS

WO91/16901  11/1991  WIPO ........................... A61K 31/70

OTHER PUBLICATIONS

"Molecular Cloning of Human Platelet Thromboxane A Synthase", Yokoyama, et al. *Biochem & Biophys. Res. Comm.*, vol. 178, No. 3, 1991, pp. 1479–1484.
J. Milligan et al. J. Med. Chem. 36(14) ('93) 1923–37.
B. Monia et al. J. Biol. Chem. 267 (28) ('92) 19954–62.
W. James Antiviral Chem & Chemosler. 2(4) ('91) 191–214.
E. Uhlumann et al. Chem. Rev. 90(4) ('90) 543–84.
B. Tseng et al. Cancer Gene Therapy 1 (1) ('94) 65–71.
C. Siena et al. Science 261 ('93) 1004–12.
P. Weszermann et al. Biomed. Biochim Acra. 48('89) 85–93.
E. Uhlmann et al. Chemical Reviews, vol. 90#4 (Jun. '90) pp. 543–584.
B. Tseng et al. Cancer Gene Therapy, vol. #1 (Mar. '94) pp. 65–71.
C. Stein et al. Science, vol. 261 (20 Aug. '93) pp. 1004–1012.
R. Weiss. Science News, vol. 139 (Feb. 16, 1991) pp. 108–109.
P. Wessermann et al. Biowed. Biochim. Aeta, vol. 48 ('89) pp. 85–93.
D. DeWitt et al. J. Biol Chem., vol. 265 #9 (25 Mar. '90) pp. 5192–5198.
M. K. O'Banion PNAS, vol. 89 (Jun. '92) pp. 4888–4892.
G. Funk et al. FASEB Journals, vol. 5 ('91) pp. 2304–2312.
T. H1. et al. PNAS, vol. 89 (Aug. 1992) pp. 7384–7388.

*Primary Examiner*—Charles C. P. Rories
*Attorney, Agent, or Firm*—Calfee, Halter & Griswold LLP

[57] ABSTRACT

The present invention provides a new antisense oligonucleotides for the treatment of premature labor, premature rupture of the fetal membranes, premature cervical dilation and effacement, preeclampsia, endometriosis, rheumatoid arthritis, ARDs, and glomerulitis. The drugs are antisense oligonucleotides which attenuate the expression of either the mRNA encoding the cyclooxygenase protein or the mRNA encoding the thromboxane $A_2$ synthase protein. Once the mRNA encoding for cyclooxygenase is inhibited, the production of cyclooxygenase is inhibited thereby inhibiting the production of the cyclooxygenase products such as prostaglandins and thromboxane. Thus, the antisense oligonucleotides provide novel therapy for the treatment of diseases involving cyclooxygenase products, prostaglandins and thromboxane metabolism. Such diseases include immunological, reproductive, cardiovascular, dermatologic, central nervous system disorders in which the release of cyclooxygenase products effects the genesis and progression of the disease. A second object of the invention is to provide new reagents for the research and study of the diseases involving cyclooxygenase products.

32 Claims, 6 Drawing Sheets

ANTISENSE OLIGONUCLEOTIDES TO SUPPRESS EICOSANOID FORMATION

This application is a continuation of application Ser. No. 08/170,089 filed on Dec. 17, 1993, now abandoned.

BACKGROUND OF THE INVENTION

Prostaglandins are synthesized in mammals, including humans and are involved in inflammatory disease. Prostaglandins induce/contribute to a myriad of conditions, including the changes in vascular permeability leading to tissue edema and swelling, biochemical changes in the production of extracellular matrix degrading enzymes, such as fibroblast collagenase and elastase, fever and pain. Prostaglandins alter the contractile properties of vascular and non-vascular smooth muscle, leading to vasodilatation, vasoconstriction, uterine contractions, and bronchospasm.

The release of arachidonic acid from cellular membrane phospholipids and the subsequent production of eicosanoids such as cyclooxygenase products and lipoxygenase products is a hallmark feature of nearly all inflammatory diseases. Free arachidonic acid is the obligate precursor of cyclooxygenase, and its products. Under unstimulated cellular conditions, nearly all arachidonic acid is esterified in membrane phospholipids and is unavailable for eicosanoid biosynthesis. However, when a cell encounters certain extracellular stimuli, phospholipase $A_2$ cleaves arachidonic acid from the phospholipid, thereby permitting the arachidonic acid to be converted into prostaglandins by cyclooxygenase.

Once liberated, the bifunctional enzyme, cyclooxygenase, catalyzes the formation of prostaglandin (hereinafter "$PGG_2$") by a bis-cyclooxygenation reaction. $PGG_2$ then undergoes a peroxidation reaction to form prostaglandin $H_2$ (hereinafter "$PGH_2$") which is the immediate precursor for all subsequent prostaglandin synthetic reactions. In certain cell types, primarily platelets in which thromboxane ($TxA_2$) is the major arachidonic acid metabolite, thromboxane synthase converts $PGH_2$ into thromboxane. Thromboxane is a potent vasoconstrictor and involved in vasoconstriction, coagulation, and preeclampsia. Other cell types, such as endothelial cells, synthesize mainly prostacyclin ($PGI_2$) which is produced from $PGH_2$ via prostacyclin synthase.

Box 1

```
PATHWAY FOR PROSTAGLANDIN BIOSYNTHESIS
         Membrane Phospholipids
        (Esterified Arachidonic Acid)
                    ↓
              Phospolipase A₂
                    ↓
            Free Arachidonic Acid
                    ↓
               Cyclooxygenase
                    ↓
                  PGG₂
                    ↓
      PGI₂ ← —— PGH₂ —— → TxA₂
             ↙     ↓
         PGF₂α   PGE₂   PGD₂
```

Prostaglandin $E_2$ and prostaglandin $F_{2\alpha}$, hereinafter "$PGE_2$" and "$PGF_{2\alpha}$" are the stimulators of uterine contractions and cervical dilatation and effacement which culminate in labor and delivery of the fetus at term. Keirse, M. J. N. C. "Eicosanoids in Human Pregnancy and Parturition", *Eicosanoids in Reproduction*, Mitchell, M. D., ed. 1990; CRC Press, Boca Raton, pp. 199–222.

The levels of $PGE_2$ and $PGF_{2\alpha}$ and their metabolites are also increased in the amniotic fluid of women in preterm labor with clinical signs of infection and are believed to be a causative factor of pre-term labor, Romero, R., Avila, C., and Sepulveda, W. "The Role of Systemic and Intrauterine Infection in Preterm Labor In: Preterm Birth: Causes, Prevention, and Management," 2d. ed., Fuchs, A. -R., Fuchs, F., and Stubblefield, P. G., eds., MacGraw-Hill, Inc., New York, 97–136. Preterm labor occurs in approximately 8–9% of all pregnancies, but accounts for 80% of perinatal morbidity and mortality in the United States. The cost of caring for premature infants who require long-term hospitalization can be as much as $500,000 per infant. Moreover, many of these babies suffer long-range medical problems as a result of their prematurity.

Currently there are several categories of tocolytic agent for the treatment of premature uterine contractions. These drugs include β-sympathomimetics such as ritodrine and terbutaline, calcium channel antagonists and the prostaglandin synthase inhibitor indomethacin. The β-sympathomimetic agents and calcium channel blockers have proven only partially successful in arresting uterine activity in women who are in latter stages of preterm labor. Moreover, these drugs produce maternal side-effects such as tachycardia, agitation, increased cardiac output, increased plasma volume, and even a small number of maternal fatalities. In women with contraindications to the use of β-sympathomimetics, there are often no alternative therapies to offer for the treatment of preterm labor. In addition, these drugs have been associated with fetal tachycardia and other potentially harmful fetal side-effects, such as intracerebral hemorrhage. Calcium channel blockers such as nifedipine and magnesium sulfate have shown some efficacy, but also have shown untoward maternal and fetal side-effects, [Vanden Veyuer, I. and Moisek.] "Prostaglandin Synthetase Inhibitors in Pregnancy," *Obstetrical and Gynecological Survey*, 1993; 48: 493–502; Eronen, M. et al., "The Effects of Indomethacin and a β-Sympathomimetic Agent on the Fetal Ductus Arteriosus During Treatment of Premature Labor: A Randomized Double-Blind Study," *Am. J. Obstet. Gynecol.*, 1991; 164: 141–146.

Indomethacin, an irreversible inhibitor of cyclooxygenase, and thus a prostaglandin synthesis inhibitor, has shown promise in the arrest of uterine contractions. However, indomethacin readily crosses the placental barrier, and causes undesirable side-effects in the fetus, including constriction of the ductus arteriosus and pulmonary hypertension, and altered cerebral blood flow. Gamissans, O. and Balasch, J. "Prostaglandin Synthetase Inhibitors in the Treatment of Preterm Birth," *Preterm Birth: Causes, Prevention, and Management*, 2d. ed., Fuchs, A. -R., Fuchs, F., and Stubblefield, P. G., eds., MacGraw-Hill, Inc., New York, 309–332.

Thus, while a few traditional pharmacologic agents exist for the treatment of premature labor in women, each has maternal and/or fetal side-effects which significantly limit their usefulness. The obstetrician is faced with the task of attempting to combat preterm uterine contractions with inadequate therapeutic tools.

Preterm premature rupture of the fetal membranes also referred to as "PROM" (that is, the bag of waters surrounding the fetus) and premature biochemical changes, such as premature dilatation and effacement also occur with preterm labor, and usually lead to premature expulsion of the fetus. These events are also mediated by prostaglandins, specifically $PGE_2$. Rath, W. et al., "Biochemical Changes in Human Cervical Connective Tissue After Intracervical Application of Prostaglandin $E_2$," *Prostaglandins* 1993; 45: 375–380. Currently, there is no pharmacologic treatment available for the treatment of premature cervical dilatation or PROM. Once the fetal membranes are ruptured, labor and delivery of the fetus are usually inevitable. However, if PROM occurs prior to 26–27 weeks gestation, the fetus is rarely able to survive. The only current treatment for premature dilatation and effacement is surgical ligation of the cervical canal. Yet the ligation itself often leads to uterine activity and preterm delivery.

Preeclampsia, a disease associated with an increased production of $TXA_2$ and a shift in the ratio of $PGI_2$ to $TXA_2$, accounts for approximately 7% of all first pregnancies. Friedman, S. A., "Preeclampsia: A Review of the Role of Prostaglandins," *Obstet. Gynecol.*, 1988; 71: 122–137. Zeeman, G. G. and Dekker, G. A., "Pathogenesis of Preeclampsia: A Hypothesis," *Clin. Obstet. Gynecol.*, 1992; 35: 317–337. Preeclampsia is characterized by maternal hypertension, renal impairment including proteinuria, liver damage, systemic vasospasm, hypercoagulation and edema, and in severe cases, seizures and even death. Preeclampsia is the leading cause of maternal mortality in most developed nations. Preeclampsia also causes reduced uteroplacental blood flow and restricts the transfer of nutrients to the fetus. This leads to intrauterine growth retardation, fetal compromise, and often necessitates preterm delivery of the infant, which contributes to the high premature birth rate. Unfortunately, if the disease occurs during the late second or early third trimester, the fetus is too premature to survive outside the uterus. The mortality rate of these infants is extremely high.

There are very few treatments available for preeclampsia. Recently, low-dose aspirin has been used for the treatment of women who are at increased risk for developing preeclampsia. However, aspirin has not been effective at alleviating the disease symptoms once they occur. Thus, at present no palliative therapies exist for the treatment of this pregnancy complication.

Endometriosis, a condition in which the uterine lining proliferates and tissue escapes into the peritoneal cavity, is a painful and debilitating disorder which can require surgical correction and often threatens the reproductive ability of the patient. At present, hormonal therapy is used to inhibit uterine endometrial proliferation. In more severe cases, excess tissue is removed surgically. However, neither of these treatments relieve the painful effects of excess prostaglandin production by the endometrial tissues.

Rheumatoid arthritis is a chronic inflammatory disease localized to joint surfaces and characterized by synovial fibroblast proliferation, degradation of bone extracellular matrix, joint swelling and crippling pain. Lefer, A. M., "Eicosanoids as Mediators of Ischemia and Shock," *Fed. Proc.*, 1985; 44: 275–280. $PGE_2$ has been shown to stimulate the production of collagenase by isolated synoviocytes and elicits bone matrix degradation by osteoclasts. Synovial cells isolated from rheumatoid arthritis patients produce approximately ten times more $PGE_2$ than cells from normal patients. Current therapies to treat rheumatoid arthritis rely on NSAIDS such as aspirin, ibuprofin and indomethacin and local administration of glucocorticoids such as dexamethasone and hydrocortisone to reduce joint pain and swelling. However, these agents cause several side-effects, chiefly gastric upset. Long-term glucocorticoid use causes liver and cardiovascular damage and loss of bone mass.

Adult respiratory distress syndrome (ARDS) and shock is a rare, but life threatening condition which can be precipitated by severe systemic infection, traumatic injury or shock and is characterized by acute endothelial cell damage in the lung, and in severe cases respiratory collapse and death. Proinflammatory cytokines, for example, interleukin-1, and tumor necrosis factor-α, (TNF-α) are thought to be the primary mediators of ARDS and they are proposed to act via arachidonic acid metabolites and platelet-activating factor. $PGI_2$ and $PGE_2$ cause increased vascular permeability and interstitial edema within the lung parenchyma and accumulation of extravasated fluid and proteins in the alveolar space, while $PGF_{2\alpha}$ and thromboxane cause vasoconstriction and pulmonary hypertension. $PGE_2$ is also a modulator of neutrophil and monocyte chemotaxis to the lung. In addition, these patients often develop systemic hypotension, leading to compromise of multiple organ systems. Thromboxane also leads to platelet activation and adhesion to microvascular wall, precipitating thrombosis and ischemia. Animal models of ARDS have provided evidence that cyclooxygenase inhibitors may attenuate some of the clinical manifestations of ARDS. However, since the production of prostaglandins in this disease is progressive, it is clinically difficult to use conventional anti-cyclooxygenase agents for the effective treatment of ARDS.

Glomerulonephritis is an inflammatory disease of the kidney which results in the influx of inflammatory cells, such as neutrophils and monocytes into the renal parenchyma. Macrophages which migrate to the kidney from distal sites, release a myriad of cytokines and eicosanoids, for example, $TxA_2$, leukotriene $B_4$ resulting in reduced renal blood flow. Since $TxA_2$ released by inflammatory macrophages is very deleterious to normal renal function, chronic injury may occur, ultimately leading to complete renal failure. In such cases, the patient is faced with certain long-term renal dialysis and even kidney transplantation. Traditional anti-inflammatory drugs such as non-specific anti-inflammatory drugs and glucocorticoids are usually not suitable since they cause generalized inhibition of prostaglandin biosynthesis, including inhibition of $PGE_2$ which is required for normal renal physiologic function. Lianos, E. A., "Eicosanoid Biosynthesis and Role in Renal Immune Injury," *Prostaglandins Leukot. Essent. Fatty Acids,* 1990; 41:1–12.

It would be desirable to have drugs for the premature labor, PROM, premature effacement and dilation, endometriosis, rheumatoid arthritis, ARDS and glomerulitis, that would eliminate the condition, without the side effects of conventional treatments.

SUMMARY OF THE INVENTION

The present invention provides new antisense oligonucleotides for the treatment of premature labor, premature rupture of the fetal membranes, premature dilation and effacement, preeclampsia, endometriosis, rheumatoid arthritis, ARDs, and glomerulitis. The antisense oligonucleotides which attenuate the expression of either the mRNA encoding the cyclooxygenase protein or the mRNA encoding the thromboxane $A_2$ synthetase protein. Once the mRNA encoding for cyclooxygenase is inhibited, the production of cyclooxygenase is inhibited thereby inhibiting the production of the cyclooxygenase products such as prostaglandins and thromboxane. The antisense oligonucleotide which only alleviates the production of mRNA encoding thromboxane $A_2$ synthase inhibits the production of thromboxane. Az synthetase thereby inhibiting the production of thromboxane. As a result, the production of prostaglandins is not inhibited. Thus, the antisense oligonucleotides provide novel therapy for the treatment of diseases involving prostaglandins and thromboxane. Such diseases include immunological, reproductive, cardiovascular, dermatologic, and central nervous system disorders in which the release of cyclooxygenase products effects the genesis and progression of the disease. A second object of the invention is to provide new reagents for the research and study of the diseases involving cyclooxygenase products.

DETAILED DESCRIPTION OP THE INVENTION

Figure 1:
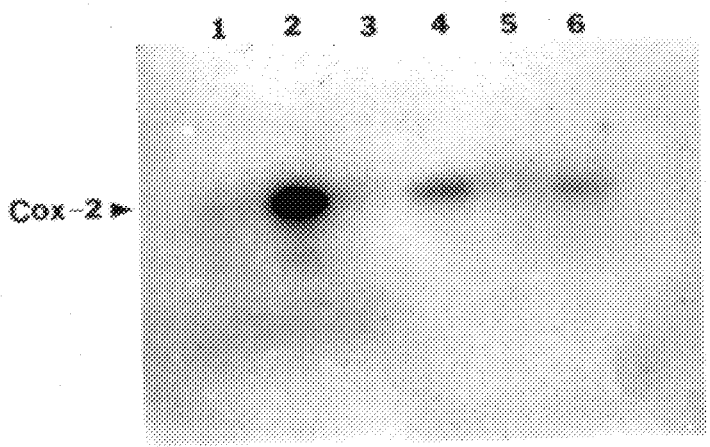
FIG. 1 is a northern blot showing the COX-2 in RNA expression in mouse 3T3 cells: treated with PMA (lane 2); preincubated with 5 $\mu$M antisense S-oligonucleotide mCOX-2.2 and treated with PMA (lane 4); preincubated with 5 $\mu$M antisense S-oligonucleotide mCOX-2.2 and no PMA (lane 3); preincubated with 10 $\mu$M antisense S-oligonucleotide mCOX-2.2 and treated with PMA (lane 6); preincubated with 10 $\mu$M antisense S-oligonucleotide mCOX-2.2 and no PMA (lane 5); and not treated with either PMA or the S-oligonucleotide (lane 1).

This invention provides antisense oligonucleotides for the treatment, diagnosis and research of diseases which involve the production and release of metabolites of arachidonic acid, including prostaglandins, thromboxane and prostacyclin. The antisense oligonucleotides are complementary to, and bind the messenger ribonucleic acids (mRNAs) which encode for either: the thromboxane A synthase; or the constitutive cyclooxygenase, referred to herein as "COX-1"; or the inducible cyclooxygenase, referred to herein as "COX-2". Several of the antisense oligonucleotides inhibit the expression of mRNAs encoding for cyclooxygenase, either COX-1 or COX-2. Suppressing the expression of the mRNA which encodes cyclooxygenase prevents the production of cyclooxygenase thereby preventing the generation of prostaglandins and thromboxane which are synthesized by the cyclooxygenase. The antisense nucleotides of the present invention do not suppress lipoxygenase products, only cyclooxygenase products. Completely or even partially suppressing the production of cyclooxygenase and the resulting metabolites is useful as a palliative therapy for the treatment of diseases in which arachidonic acid release and the production of cyclooxygenase products such as $PGE_2$, $PGF_{2\alpha}$, $PGD_2$, $PGI_2$, and thromboxane are part of the disease pathophysiology.

The antisense oligonucleotides directed to the mRNA encoding thromboxane synthase selectively suppress the production of thromboxane, while sparing other physiologically important prostaglandins. Such oligonucleotides offer a palliative treatment of glomerulonephritis by specific blockade of thromboxane release.

Antisense Oligodeoxynucleotides

The antisense oligonucleotides which are directed against the mRNA of human thromboxane $A_2$ synthase and both the constitutive and inducible forms of murine and human cyclooxygenases, were constructed from the corresponding cDNA sequences. The cDNA sequences listed in Table 1 were obtained from Genbank, an on-line computer service. Then the nucleotide sequences of the cDNAs were fed into by a microcomputer. The regions of each mRNA molecule which would provide a theoretically stable hybrid with the cognate antisense oligodeoxynucleotide were chosen based upon thermodynamic conditions using algorithms in the software OLIGO® available from National Biosciences in Minneapolis, Minn. Most of the antisense oligonucleotides contain 18 deoxynucleotides. The 18 deoxynucleotides are the preferred length in terms of stability and efficiency of uptake into cells. However, oligonucleotides containing for example, from 12 to 15 nucleotides or longer oligonucleotides, containing, for example, 20 nucleotides are also suitable. Such oligonucleotides are shown in Tables 2 and 3. The antisense oligonucleotides of the present invention are all deoxynucleotides.

Previous studies using many different mRNA targets have shown that the regions of the mRNA to which antisense oligonucleotides hybridize are critical for efficient inhibition of the desired function. Thus, the 5'-untranslated region just upstream from the ATG start codon and the 3'-untranslated region were the predominant targets for the antisense oligonucleotides. Once antisense oligonucleotides that provided thermodynamically stable hybrids with the target mRNA were designed, they and the phosphorothioate derivatives of such oligonucleotides were ordered from oligos Etc.®, Minneapolis, Minn., which produced the desired oligonucleotides according to conventional phosphoramidite chemistry. The oligonucleotides that were unmodified, are hereinafter also referred to as "N-oligonucleotides". The phosphorothioate derivative nucleotides are hereinafter also referred to as "S-oligonucleotides".

TABLE 1

Description of cDNA Sequences Used to Construct Antisense S-oligodeoxynucleotides

| Target mRNA | GenBank Accession # | cDNA Length | Coding Sequence | 5'-UTR Length | 3'-UTR Length |
|---|---|---|---|---|---|
| mCOX-1 | M34141 SEQ. ID. NO. 26 | 2757 | 37-1844 | 1-36 | 1843-2757 |
| mCOX-2 | M64291 SEQ. ID. NO. 27 | 3986 | 125-1939 | 1-124 | 1940-3986 |
| hCOX-1 | M59979 SEQ. ID. NO. 28 | 2554 | 6-1805 | 1-5 | 1806-2554 |
| hCOX-2 | M90100 SEQ. ID. NO. 29 | 3387 | 98-1912 | 1-97 | 1913-3387 |
| hTXS | M80646 | 1719 | 172-1554 | 1-171 | 1555-1719 | mCOX-1 and mCOX-2 refer to murine COX-1 and COX-2.
hCOX and hCOX-2 refer to human COX-1 and COX-2.

TABLE 2

Mouse Cyclooxygenase-2 Antisense S-oligodeoxynucleotides

| Oligo. Designation | Nucleo. Length | Start Position | Oligo. Sequence |
|---|---|---|---|
| mCOX-1.1 | 18 | 13 | 5'-GGGAGTGGATGGATGTGC-3' SEQ. ID. NO. 25 |
| mCOX-1.2 | 18 | 1864 | 5'-AAAACTCCTCCCTCCAGA-3' SEQ. ID. NO. 1 |
| mCOX-1.3 | 18 | 1904 | 5'-CCACGAAAACCCACATCA-3' SEQ. ID. NO. 2 |
| mCOX-1.4 | 18 | 1987 | 5'-CCGAAAGTGGCAAAATCA-3' SEQ. ID. NO. 3 |
| mCOX-1.5 | 18 | 16 | 5'-TCTGGGAGTGGATGGATG-3' SEQ. ID. NO. 4 |
| mCOX-2.2 | 18 | 104 | 5'-AGAGGTGGCAGCGGAGGT-3' SEQ. ID. NO. 5 |
| mCOX-2.3 | 18 | 2126 | 5'-AGAGGAATCAATGCTGAT-3' SEQ. ID. NO. 6 |
| mCOX-2.4 | 18 | 112 | 5'-GAGCATCGCAGAGGTGGC-3' SEQ. ID. NO. 7 |
| mCOX-2.5 | 18 | 2371 | 5'-TTGGACCCCTTTGTTTGA-3' SEQ. ID. NO. 8 |

Length of antisense S-oligodeoxynucleotides is in bases. Start position denotes the position of the first base of the antisense oligonucleotide within the cDNA sequence.

TABLE 3

Human Cyclooxygenase-2 Antisense S-oligodeoxynucleotides

| Antisense Oligo. Designation | Nucleo. Length | Start Position | Oligo. Sequence |
|---|---|---|---|
| hCOX-1.1 | 18 | 1 | 5'-GACTCCGGCTCATGGCGC-3' SEQ. ID. NO. 9 |
| hCOX-2.1 | 18 | 51 | 5'-GTAGGCTTTGCTGTCTGA-3' SEQ. ID. NO. 10 |
| hCOX-2.2 | 12 | 97 | 5'-CGGGCGAGCATC-3' SEQ. ID. NO. 11 |
| hCOX-2.3 | 18 | 79 | 5'-GCAGCGGCGGGCAGGGCG-3' SEQ. ID. NO. 12 |
| hCOX-2.4 | 15 | 89 | 5'-GAGCATCGCAGCGGC-3' |

TABLE 3-continued

Human Cyclooxygenase-2 Antisense S-oligodeoxynucleotides

| Antisense Oligo. Designation | Nucleo. Length | Start Position | Oligo. Sequence |
|---|---|---|---|
| | | | SEQ. ID. NO. 13 |
| hCOX-2.5 | 18 | 89 | 5'-GGCGAGCATCGCAGCGGC-3' |
| | | | SEQ. ID. NO. 14 |
| hCOX-2.6 | 15 | 97 | 5'-GCGCGGGCGAGCATC-3' |
| | | | SEQ. ID. NO. 15 |
| hCOX-2.7 | 18 | 97 | 5'-AGGGCGCGGGCGAGCATC-3' |
| | | | SEQ. ID. NO. 16 |
| hCOX-2.8 | 18 | 2037 | 5'-ATGACTCCTTTCTCCGCA-3' |
| | | | SEQ. ID. NO. 17 |
| hCOX-2.9 | 20 | 2789 | 5'-TTTTGGCGGGGTTATGGGGT-3' |
| | | | SEQ. ID. NO. 18 |

Length of antisense S-oligonucleotides is in bases. Start position denotes the position of the first base of the antisense oligonucleotide within the cDNA sequence.

TABLE 4

Human Thromboxane $A_2$ Synthase Antisense S-oligodeoxynucleotides

| Oligo. Designation | Length (nucleotide) | Start Position | Nucleotide Sequence |
|---|---|---|---|
| hTXS-1 | 18 | 54 | 5'-AACCAAGCAAACATCACA-3' |
| | | | SEQ. ID. NO. 19 |
| hTXS-2 | 18 | 94 | 5'-TTATGGGAACCGTGCTCT-3' |
| | | | SEQ. ID. NO. 20 |
| hTXS-3 | 18 | 165 | 5'-GCTTCCATCATTCCTCTG-3' |
| | | | SEQ. ID. NO. 21 |
| hTXS-4 | 18 | 1554 | 5'-TAGGGCAGATTTGGATTC-3' |
| | | | SEQ. ID. NO. 22 |
| hTXS-5 | 18 | 1701 | 5'-GGCTTTCAATCACTTCAG-3' |
| | | | SEQ. ID. NO. 23 |
| hTXS-6 | 18 | 166 | 5'-GGCTTCCATCATTTCTCT-3' |
| | | | SEQ. ID. NO. 24 |

When received from the commercial assembler, the antisense oligonucleotides were reconstituted in sterile distilled water from lyophilized stocks at working concentration of 2 mM. Since the antisense oligonucleotides were evaluated in cell cultures, the working solutions of the antisense oligonucleotide were diluted further with serum-free culture media for addition to cell cultures. In some cases, the antisense nucleotides were added to cell cultures which had been preincubated with 10 μg/ml of cationic liposomes Lipofection reagent®, available from GIBCO®/BRL, Bethesda, Md. to enhance cellular uptake. However, addition of the cationic liposomes was found to be unnecessary under most circumstances and an 18 hour preincubation with the S-oligonucleotide prior to stimulation of prostaglandin formation was sufficient for uptake of the oligonucleotides. After the cell cultures were incubated with the S-oligonucleotide being evaluated, cell cultures were stimulated with an agent to promote the production of the thromboxane or the prostaglandin or both. The effect of the antisense oligonucleotides were evaluated in several different ways. At the end of each stimulation period, the media were collected from the cells and the thromboxane or the prostaglandin or both, were measured by specific radioimmunoassay. The antisera and protocol for these assays have been described in Fertel et al., 1981, *Biochem. Biophys. Res. Comm.*, 102: 1028–1033; Kniss et al., 1992, *Prostaglandins*, 44: 237–244; Kniss et al., 1993, *Prostaglandins*, 45: 27–33. The COX mRNA was determined by preparing northern blots by harvesting the cells, extracting the total mRNA, fractionating the RNA on a 1% agarose gel, blotting the appropriate fraction onto nylon membranes, probing the blots with a [$^{32}$P] labelled cDNA probe encoding the COX cDNA. Alternatively, the proteins were extracted from cells with 1% Triton X-100, and western blots were prepared by fractionating the proteins on a 10% polyacrylamide gel, transferring to nitrocellulose and then probing with an antibody specific for enzyme being measured. The probe was then detected by standard methods.

The Antisense Oligonucleotides as Cyclooxygenase Inhibitors

Inhibition of Cyclooxygenase in Fibroblasts

Mouse NIH 3T3 cells (fibroblasts) were used as a model system for the evaluation of the antisense oligonucleotides on prostaglandin production by fibroblasts. Prostaglandin is formed by fibroblasts isolated from a variety of tissue sources and disease processes, for example, synovial cells from rheumatoid arthritis patients, interstitial fibroblasts from patients with adult respiratory distress syndrome [ARDS], cervical incompetence. The 3T3 cells are an immortalized population of cells which manifest many properties of mouse fibroblasts maintained in primary culture. To establish a culture of 3T3 cells, they were seeded into 48-well plates at a concentration of $2 \times 10^5$/well which had been precoated with type I collagen, in Dulbecco's Modified Eagle Media/Ham's F12+10% newborn calf serum and grown at 37° C. in 5% $CO_2$/95% air.

To evaluate the antisense oligonucleotides for either prostaglandin suppression or mCOX mRNA suppression, the 3T3 cells were seeded into 35 mm dishes ($2 \times 10^6$/dish) in Ham's F12\Dulbecco's Modified Eagle Media supplemented with 10% newborn calf serum. After 24 hours, the cells were incubated in 0.25 serum-free medium for 18 hours with the desired concentration of the desired mCOX antisense S-oligonucleotide. Control cells received vehicle only during the preincubation. The cells were then challenged with 30 nM phorbol 12-myristate 13-acetate, hereinafter also referred to as "PMA", for 4 hours. PMA is an agent known to promote prostaglandin formation.

The determine the effect of the antisense S-oligonucleotide mCOX-2.2 on the COX-2 mRNA, the 3T3 cells were incubated in 0.25 serum-free medium for 18 hours with either 5 or 10 μM antisense S-oligonucleotide mCOX-2.2. Total RNA was prepared, fractionated on a 1% agarose gel, and blotted onto nylon membranes. The blots were probed with a [$^{32}$P] labelled cDNA probe encoding the murine COX-2 cDNA. The TIS10 probe was donated by Dr. Harvey Herschman at UCLA. The Northern blot is shown in FIG. 1.

As shown, lanes 5 and 6 of FIG. 1, 10 μM of the antisense S-oligonucleotide mCOX-2.2 significantly suppressed the formation of the mRNA encoding COX-2. Moreover, there is a dose-dependent diminution in COX-2 mRNA expression (arrowhead) in cells treated with 5 μM of the antisense S-oligonucleotide mCOX-2.2, shown in lanes 3 and 4, or 10 μM S-oligonucleotide shown in lanes 5 and 6, as compared to control cells which are shown in lane 2. Lanes 3 and 5 received only the S-oligonucleotide and no PMA, that is they were not stimulated; therefore, no expression of COX-2 mRNA was expected in these cells.

The antisense S-oligonucleotide mCOX-2.4 was evaluated for suppressing prostaglandin production in the same culture system as described above. Either 5 μM or 10 μM of the antisense S-oligonucleotide, mCOX-2.4 was added to the cultures. $PGE_2$ production was measured by specific radioimmunoassay.

Figure 2:
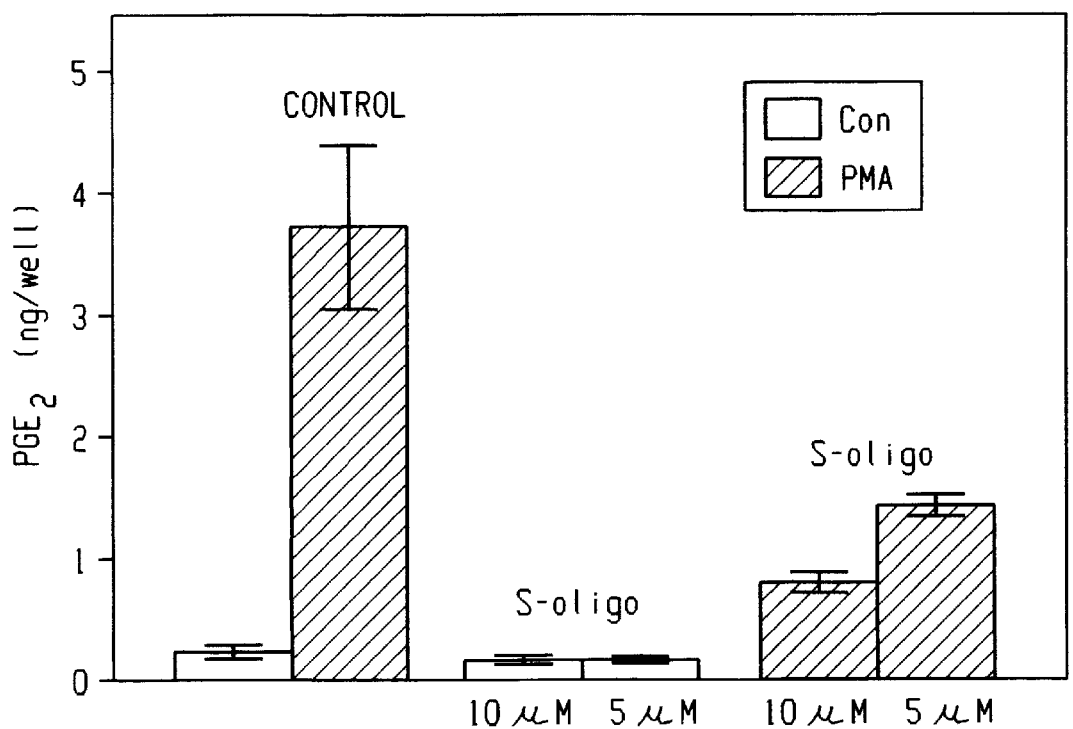
FIG. 2. is a graph demonstrating mCOX-2.4 antisense oligonucleotide suppression of $PGE_2$ production in a dose-dependent manner. The cells were preincubated for 18 hours with either 5 or 10 $\mu$M of S-oligonucleotide corresponding to the mCOX-2.4 sequence. Cells challenged with PMA are represented by cross-hatched bars. Cells not challenged with PMA are represented by open bars. The data are mean±SEM of 4 replicates per condition.

As shown in FIG. 2, the 10 μM dosage significantly suppressed the production of $PGE_2$. Again, a dose-dependent relationship was established; the 5 μM dose was only half as effective as the 10 μM dose at inhibiting $PGE_2$ production.

Figure 3:
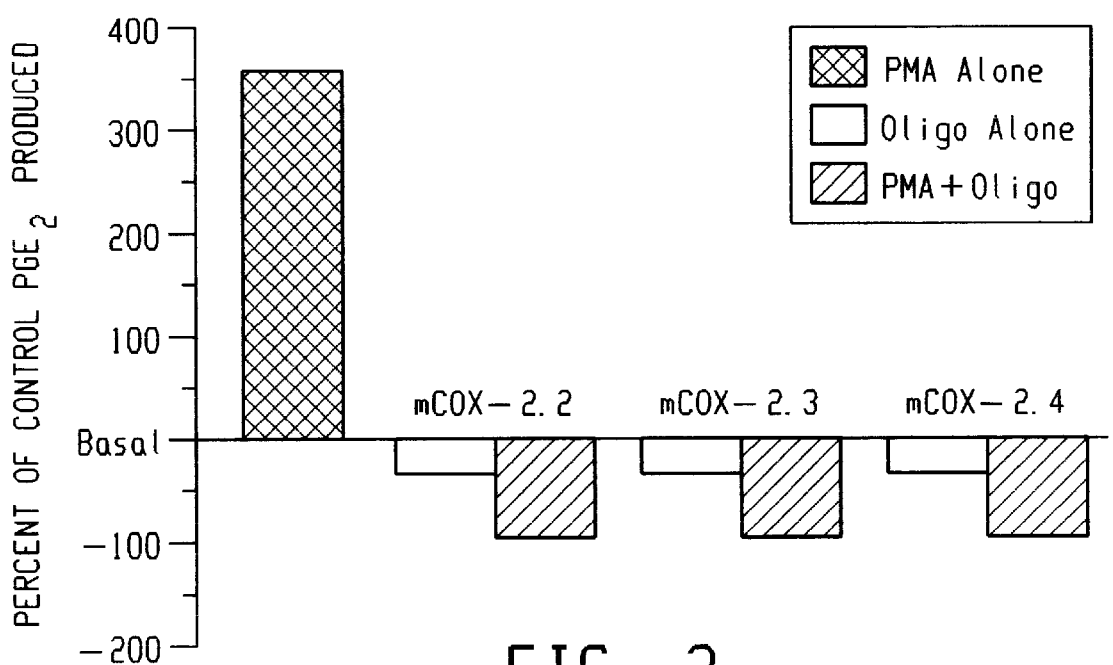
FIG. 3. is a graph demonstrating mCOX-2.2, mCOX-2.3, and mCOX-2.4 antisense S-oligonucleotides suppression of $PGE_2$ production in PMA stimulated 3T3 cells. The cells challenged with PMA are represented by closed and cross-hatched bars. Cells not challenged with PMA are represented by open bars. The data are mean±SEM of 8 replicates per condition.

The relative ability to suppress prostaglandin synthesis of three S-oligonucleotides, mCOX-2.2, mCOX-2.3, and mCOX-2.4, was determined. Each 3T3 cell cultures received 5 μM of one of the S-oligonucleotides for 24 hours, followed by a 4-hour stimulation period with 30 nM PMA. Control cells received 0.01% vehicle, dimethylsulfoxide, also referred to herein as "DMSO". The results are shown in FIG. 3 which reflects a representative experiment and is the mean of 8 replicates per condition. The data are expressed as the % of control $PGE_2$ production.

As shown in FIG. 3, the basal $PGE_2$ production by unstimulated cells is shown on the horizontal line. The PMA treatment alone stimulated a 360% increase in $PGE_2$ synthesis in the 3T3 cells relative to basal levels in untreated cells. When control cells were pretreated with S-oligonucleotide, however, there was a complete suppression of basal $PGE_2$ production as shown by open bars in FIG. 3. In PMA-treated cells there was also a complete suppression of PMA-stimulated $PGE_2$ production.

The ability of the antisense nucleotides mCOX-2.2 and mCOX-2.3 were also determined using the above culture system. Varying doses as listed in Table 5 of each nucleotide were administered to the cultures. The resulted are presented in Table 5.

TABLE 5

Dose-dependent Suppression of $PGE_2$ Production in Mouse 3T3 Fibroblasts by mCOX-2.2 and mCOX-2.3

|  | PMA | Antisense Oligonuc. mCOX-2.2 | $PGE_2$ (pg/well) |  | $PGE_2$ (pg/well) |
|---|---|---|---|---|---|
| Control | — | — | 23 ± 4 | Control | 25.8 ± 0 |
| Control | yes | — | 1,360 ± 32 | PMA | 1,410 ± 104 |
|  |  | mCOX-2.3 |  |  |  |
| Treated | yes | 40 μM | * | 40 μM | * |
| Treated | yes | 20 | 83.5 ± 5.8 | 20 | 302 ± 8.5 |
| Treated | yes | 10 | 386 ± 5.8 | 10 | 387 ± 10.9 |
| Treated | yes | 5 | 768 ± 87.4 | 5 | 453 ± 71.3 |
| Treated | yes | 1 | 1,071 ± 13 | 1 | 877 ± 45.3 |
| Treated | yes | 0.1 | 1,302 ± 97 | 0.1 | 1,075 ± 152 |

*below detectable limit. The limit of detection for the radioimmunoassay was <1.56 pg/100 μl.

As shown in Table 5, both the mCOX-2.2 and mCOX-2.3 completely suppress the prostaglandin formation at doses of 40 μM, and significant suppression occurs with 10 μM. Again, the dose dependent relationship is apparent.

The relative efficacy of the unmodified, N-oligonucleotide in comparison to phosphorothioate derivative, S-oligonucleotide was determined for the inhibition of mCOX-2 and suppression of $PGE_2$ production in 3T3 cell cultures. The cultures were prepared as described above and 10 μM of either the S-oligonucleotide or the N-oligonucleotide were added. The cultures were then exposed to 30 n PMA.

Figure 4:
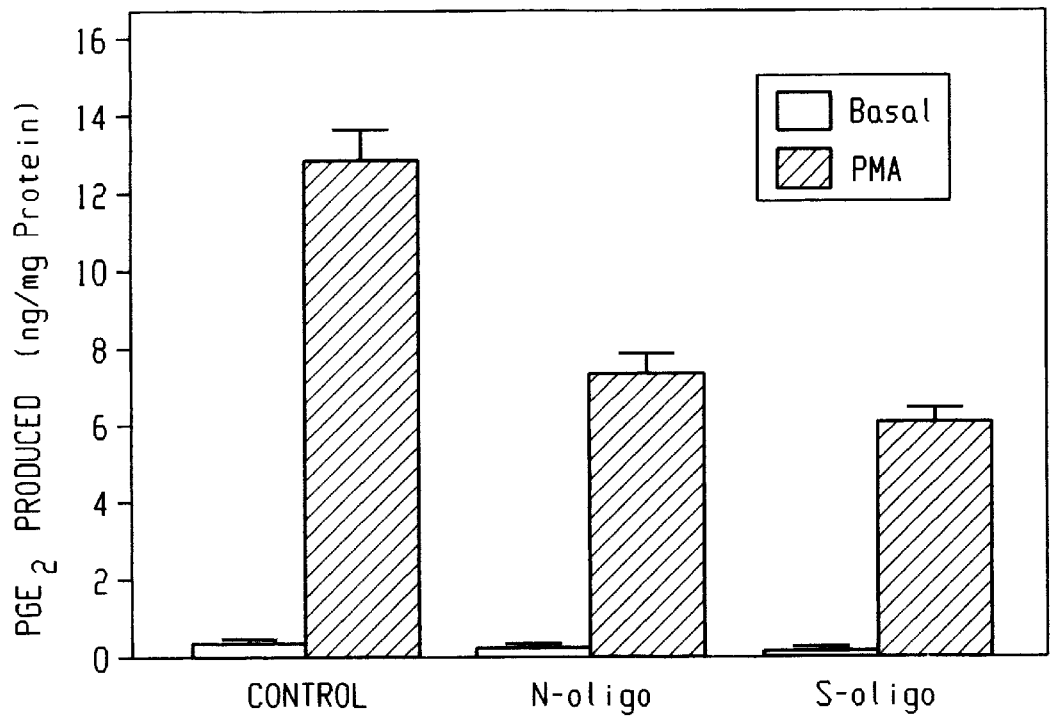
FIG. 4. is a graph demonstrating mCOX-2.4 antisense oligonucleotides attenuating $PGE_2$ production in stimulated mouse 3T3 cells. Cells were preincubated for 18 hours with 10 $\mu$M of either N-oligonucleotide or S-oligonucleotide corresponding to the mCOX-2.4 sequence. Cells challenged with PMA are represented by cross-hatched bars. Cells not challenged with PMA are represented by open bars. The data are the mean±SEM of 4 replicates per condition and are representative of 2 experiments.

As shown in FIG. 4, the mCOX-2.4 antisense S-oligonucleotide was more effective than the unmodified N-oligonucleotide targeted against the same mRNA. The $PGE_2$ production in the S-oligonucleotide treated cells was reduced by 52% of the level of control cells, while the N-oligonucleotide treated cells reduced $PGE_2$ production by 43% of control levels. Neither the S-oligonucleotide nor N-oligonucleotide treated cells appeared to differ from control cells with respect to cellular viability as assessed by trypan blue exclusion. In addition, the basal level synthesis of $PGE_2$ was completely abolished in 3T3 cells when treated with S-oligonucleotide mCOX-2.4.

Cyclooxygenase Inhibition In Amnion-Derived Cells

Four human antisense S-oligonucleotides directed to different regions of the human inducible COX mRNA designated hCOX-2 were evaluated for their ability to suppress $PGE_2$ production in PMA stimulated amnion-derived WISH cells. The WISH cells are an accepted a model system for the production of $PGE_2$ in the setting of preterm labor. See: Mitchell, M. D, et. al "Immunologic Aspects of Preterm Labor", *Seminars in Perinatology*, 1991; 15:210–224; Kniss, D. A. et. al, "Evidence of a Role for Protein Kinase C in Epidermal Growth Factor-Induced Prostaglandin $E_2$ Synthesis in Amnion Cells," *Am. J. Obstet. Gynecol.*, 1990; 163: 1883–1890. It appears that the amnion cell is a major contributor to the $PGE_2$ that is involved in the onset of labor at term and in preterm labor. WISH cells are an immortalized cell line derived from a normal human amnion membrane and retains nearly all of the properties of human amnion cells maintained in primary culture. The cells were cultured in Dulbecco's Modified Eagle Media/Ham's F12 Media (1:1) supplemented with 10% newborn calf serum, 1 mM sodium pyruvate, 2 mM L-glutamine, and 50 μg/ml gentamicin sulfate. The cells were grown at 37° C. in 5% $CO_2$/95% air. For the antisense experiments, the WISH cells were seeded into 48-well plates at $2 \times 10^5$/well in the culture medium described above and grown for 1 day at 37° C. in 5% $CO_2$/95% air. WISH cells were preincubated for 18 hours with 5 μM of either hCOX-2.1, hCOX-2.2, hCOX-2.8, or hCOX-2.9 antisense S-oligonucleotides. The cells were then challenged for 4 hours with 30 nM PMA. $PGE_2$ production was measured by specific radioimmunoassay.

Figure 5:
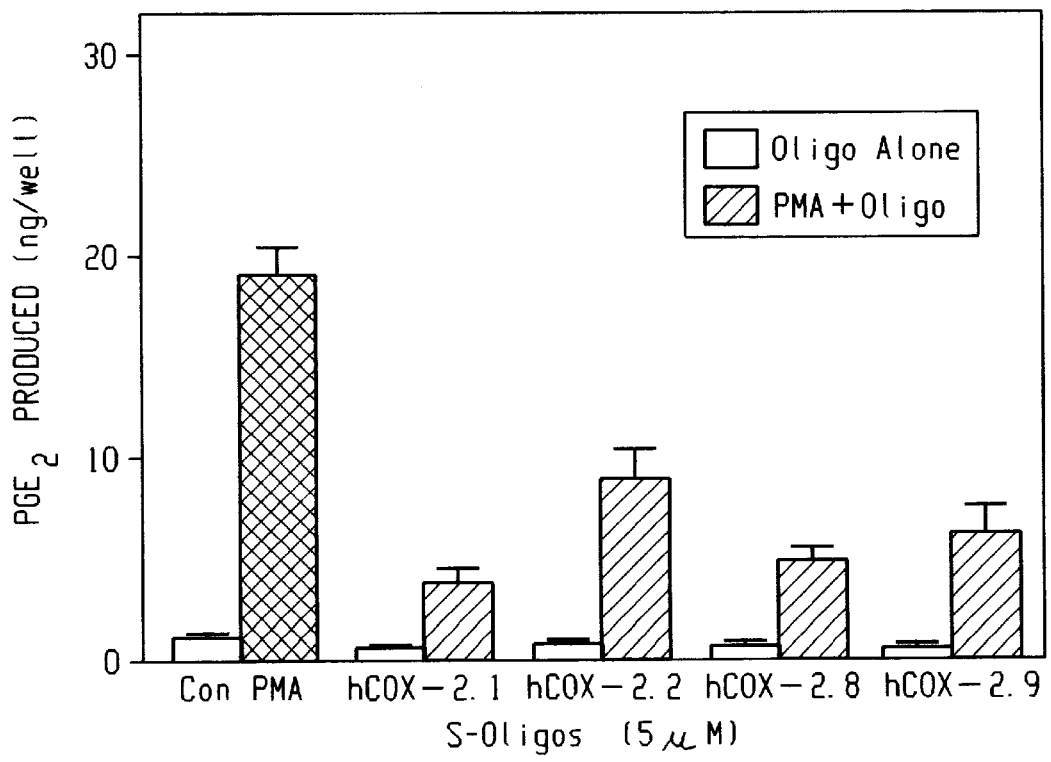
FIG. 5. is a graph demonstrating hCOX-2.1, hCOX-2.2, hCOX-2.8, and hCOX-2.9 antisense S-oligonucleotide suppression of $PGE_2$ production in PMA simulated WISH cells. The cells challenged with PMA are represented by solid bars and by cross-hatched bars. Cells not challenged with PMA are represented by open bars. The data are mean+SEM of 4–8 replicates per condition.

FIG. 5 shows that all four S-oligonucleotides effectively inhibited PMA-induced $PGE_2$ synthesis with the following order of efficacy: hCOX-2.1>hCOX-2.8>hCOX-2.9>hCOX-2.2.

The hCOX-2.9 antisense S-oligonucleotide directed to hCOX-2 was evaluated in a dose-response study in which varying doses of from 0.1 to 40 μm of hCOX-2.9 were added to the wish cell cultures. The results are shown in FIG. 6.

Figure 6:
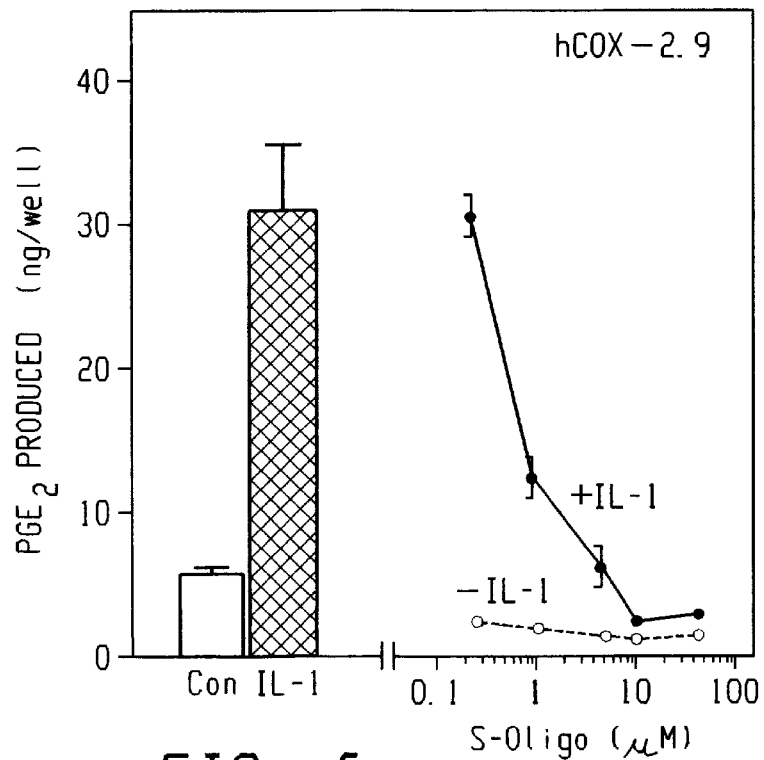
FIG. 6. is a graph demonstrating hCOX-2.9 antisense S-oligonucleotide suppression of $PGE_2$ production in a dose-dependent manner in WISH cells. Cells challenged with interleukin-1$\beta$ are represented by closed bars. Cells not challenged with interleukin-1$\beta$ are represented by open bars. The data are mean±SEM of 4–8 replicates per condition and are representative of 2 experiments.

As shown in FIG. 6, the antisense S-oligonucleotide hCOX-2.9 produced a greater than 50% suppression of $PGE_2$. A maximal suppression was seen at 10 μM. Moreover, the antisense S-oligonucleotides completely suppressed basal $PGE_2$ synthesis.

To verify that the inhibition by the antisense oligonucleotide was specific rather than non-specific, a sense S-oligonucleotide corresponding to hCOX-2.9 was tested in the WISH cell. There was no statistically demonstrable inhibition of WISH cell $PGE_2$ production by the sense S-oligonucleotide unless high concentrations were used (≧40 μM), at which point there was modest inhibition of $PGE_2$ biosynthesis.

To determine whether antisense S-oligonucleotides directed against human COX-2 mRNA alter the expression of COX-1, enzyme amnion-derived human WISH cells were plated into 35 mm dishes ($2\times10^6$/dish) in F12\Dulbecco's Modified Eagle Media supplemented with 10% newborn calf serum. After 24 hours, the cells were incubated in serum-free medium for 18 hours with 10 μM of the antisense S-oligonucleotide hCOX-2.1. Control cells received vehicle only during the preincubation. The cells were then challenged with 10 ng/ml of interleukin-1β for 4 hours, extracted with 1% Triton X-100 and the proteins were fractionated on a 10% polyacrylamide gel. Proteins were transferred to nitrocellulose and then probed with an antibody specific for COX-1. The western blot is show in FIG. 7.

Figure 7:
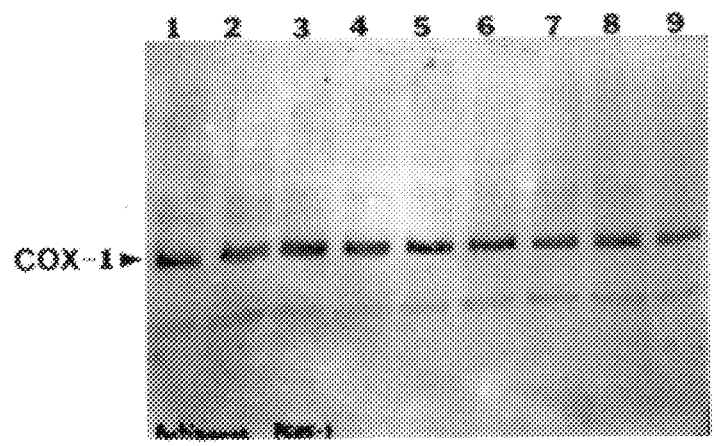
FIG. 7 is a western blot showing the COX protein expression in WISH cells: treated with interleukin-1$\beta$ (lane 2); preincubated with 10 $\mu$M antisense S-oligonucleotide hCOX-2.1 and treated with interleukin-1$\beta$ (lanes 3–9); and not treated with either interleukin-1$\beta$ or S-oligonucleotide (lane 1).

As shown in FIG. 7, the S-oligonucleotide hCOX-2.1, which suppresses the expression of the COX-2 protein, does not suppress the expression of the COX-1 protein. Thus, the antisense nucleotides specifically bind the designated mRNA.

Cyclooxygenase Inhibition in Endometrial Stromal Cells and Amnion Derived Cells

Figure 8:
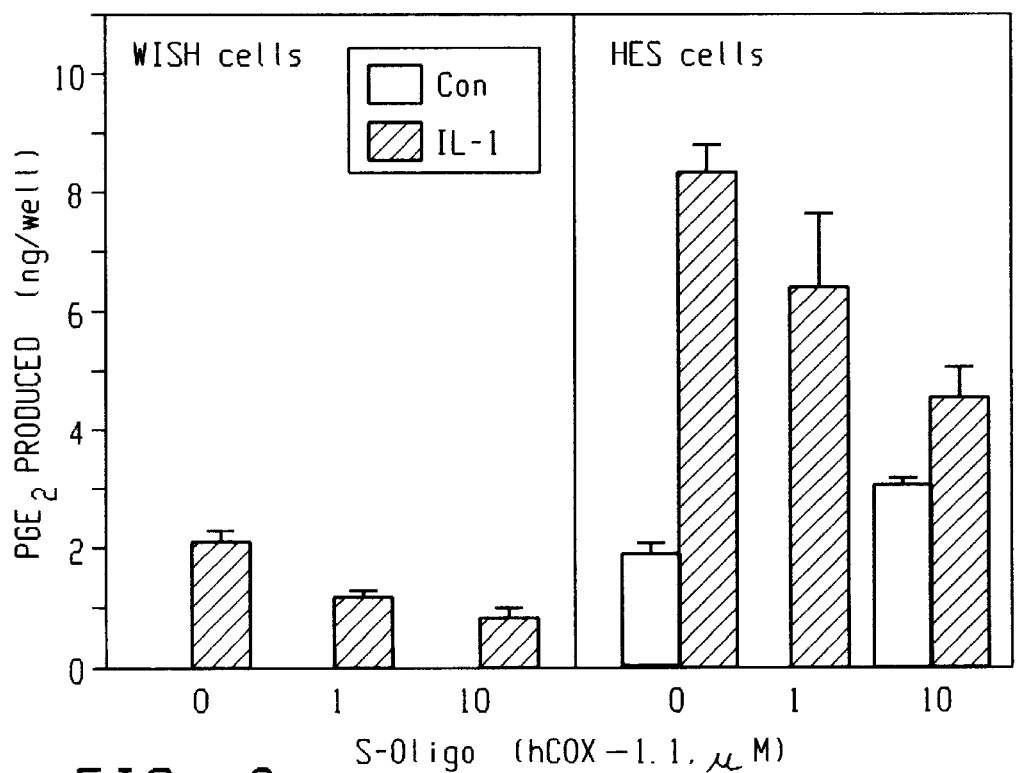
FIG. 8. is a graph demonstrating hCOX-1.1 antisense S-oligonucleotide suppression of $PGE_2$ production in WISH cells and in HES cells. Cells not challenged with interleukin-1$\beta$ are represented by open bars and cells challenged with interleukin 1$\beta$ are represented by cross-hatched bars. The data are mean±SEM of 4 replicates per condition.

To determine whether antisense S-oligonucleotides directed against hCOX-1 inhibit $PGE_2$ formation, WISH cells and HES cells were used. Human endometrial stromal (HES) cells were used as a model system for the production of $PGE_2$ and PGF2α by the uterine decidua in the setting of preterm labor, menstrual cramping and endometriosis. The human pregnancy endometrium (decidua) lining the uterine cavity and in contact with the placenta is a major contributor to the $PGF_{2\alpha}$ which is responsible for myometrial contractions during labor. The HES cells were developed as a model system in which to study the uterine contribution to PG production. This cell line was prepared following a uterine biopsy obtained from a women undergoing a hysterectomy for non-malignant uterine disease. The endometrial surface was removed with a scalpel and dissociated into as a single-cell suspension with trypsin. The cells were grown in medium 199 supplemented with 10% fetal bovine serum and 50 µg/ml gentamicin. The cultures were split once per week until a single cell type exhibiting epithelial properties remained. The cell line obtained from this biopsy specimen has retained many of the properties of human endometrial/decidual cells maintained in primary culture. The cells were grown at 37° C. in 5% $CO_2$/95% air. For the antisense oligonucleotide evaluations, the cells were seeded into 48-well plates at $2\times10^5$/well in the culture medium described above and grown for 1 day at 37° C. in 5% $CO_2$/95% air. The cultures were preincubated for 18 hours either with 0, 1, or 10 µM hCOX-1.1, followed by a 4 hour stimulation with 10 ng/ml interleukin-1β. $PGE_2$ synthesis was measured by specific radioimmunoassay. Antisense S-oligonucleotide hCOX-1.1 inhibited WISH cell and HES cell $PGE_2$ synthesis in a dose-dependent fashion as shown in FIG. 8. However, hCOX-1.1 appeared somewhat more effective in WISH cells than HES cells. This may be due, in part, to the much greater synthesis of $PGE_2$ by HES cells when stimulated by IL-1β when compared to WISH cells.

Suppression of COX-2 Protein in Amnion-Derived WISH Cells.

Amnion-derived human WISH cells were plated into 35 mm dishes ($2\times10^6$/dish) in F12\Dulbecco's Modified Eagle Media supplemented with 10% newborn calf serum. After 24 hours, the cells were incubated in serum-free medium for 18 hours with either 5, 10, 20 or 40 µM of the antisense S-oligonucleotide hCOX-2.1. Control cells received only vehicle during the preincubation period. The cells were then stimulated for 4 hours with interleukin-1β and proteins were extracted with 1% Triton X-100, fractionated by polyacrylamide gel electrophoresis, and blotted onto nitrocellulose membranes. The membranes were probed with rabbit polyclonal antibodies to mouse COX-2 and were subsequently detected by incubation with goat anti-rabbit IgG conjugated to alkaline phosphatase followed by development with NBT/BCIP. The western blot shown in FIG. 9 has Lane 1, control; lane 2, IL-1β alone; lane 3, IL-1β+5 µM S-oligonucleotide; lane 4, IL-1β+10 µM S-oligonucleotide; lane 5, IL-1β+20 µM S-oligonucleotide; and lane 6, IL-1β+40 µM S-oligonucleotide.

Figures 9, 10:
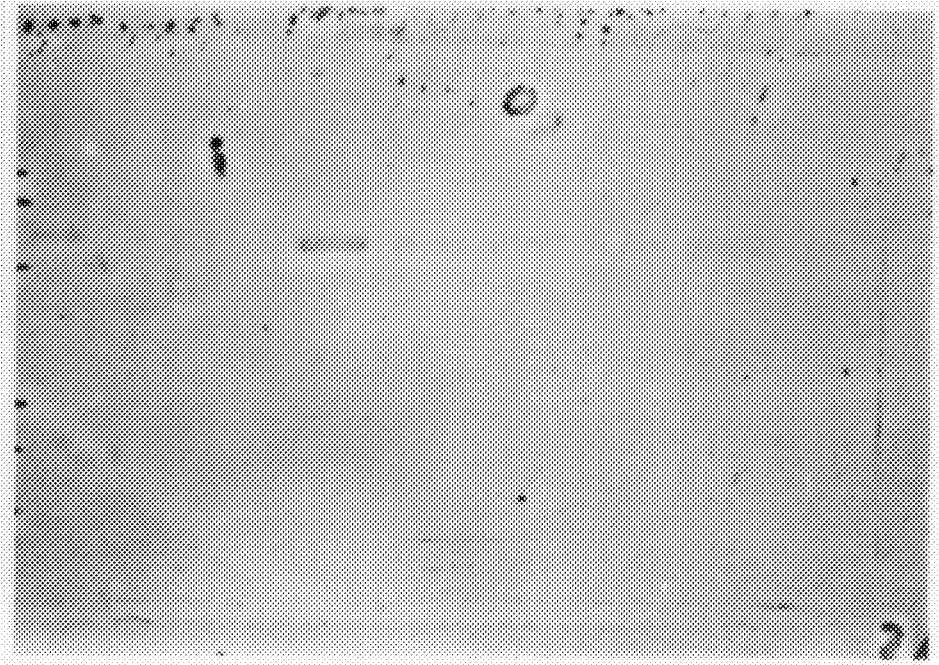
FIG. 9 is a western blot showing the COX-2 protein expression in wish cells: treated with interleukin-1$\beta$ (lane 2); preincubated with 5 $\mu$M antisense S-oligonucleotide hCOX-2.1 and treated with interleukin-1$\beta$ (lane 3); preincubated with 10 $\mu$M antisense S-oligonucleotide hCOX-2.1 and treated with interleukin-1$\beta$ (lane 4); preincubated with 20 $\mu$M S-oligonucleotide hCOX-2.1 and treated with interleukin-1$\beta$ (lane 5); preincubated with 40 $\mu$M S-oligonucleotide hCOX-2.1 and treated with interleukin 1$\beta$; and not treated with either interleukin-1$\beta$ or the S-oligonucleotide (lane 1).
FIG. 10 is a northern blot showing the COX2 mRNA expression in mouse macrophages: treated with LPS (lane 2); preincubated with 10 $\mu$M antisense S-oligonucleotide mCOX-2.2 and treated with LPS (lane 3); and not treated with either LPS or the S-oligonucleotide (lane 1).

As shown in FIG. 9 the S-oligonucleotide hCOX-2.1 decreased the expression of the COX-2 protein (lanes 3–6) compared to cells treated with interleukin-1β alone (lane 2).

Suppression of Endotoxin-Induced COX-2 mRNA Expression in Mouse Peritoneal Macrophages.

Mouse macrophages were plated into 6-well plates ($3\times10^6$/well) in Dulbecco's modified Eagle's medium+10% fetal bovine serum. After 24 hours, the cells were incubated in serum-free medium for 18 hours with 10 µM of the antisense S-oligonucleotide mCOX-2.2. Control cells received vehicle only during the preincubation. The cells were then challenged with 10 µg/ml of LPS (lanes 2 and 3) for 4 hours and total RNA was prepared and fractionated on a 1% agarose gel. After blotting the RNAs onto nylon membrane they were probed with a [$^{32}$P] labeled cDNA probe encoding the murine COX-2 cDNA. The northern invention blot is shown in FIG. 10.

As shown in FIG. 10, there is a nearly complete elimination of COX-2 mRNA expression in LPS cells pretreated with antisense S-oligonucleotide, shown in lane 3, compared with control cells which were treated with LPS, shown in lane 2.

Thromboxane $A_2$ Synthase Inhibition in Placental Cells

To determine whether antisense S-oligonucleotides directed against the mRNA encoding human thromboxane $A_2$ synthase (TxS), inhibited production of thromoxane, the placental cell line $ED_{27}$ was used as a model system. The $ED_{27}$ cells were established as an immortalized cell line of trophoblasts isolated from human first trimester chorionic villi. These cells retain nearly all of the properties of human trophoblasts maintained in primary culture and have served as an excellent model for studies of placental cell physiology. These cells make large amounts of $PGE_2$, $PGF_{2\alpha}$, and thromboxane in response to a variety of cytokines including interleukin-1β.

The cells were grown in F12/DMEM supplemented with 15% fetal bovine serum, glutamine, pyruvate and gentamicin at 37° C. in 5% $CO_2$/95% air. Cells were cultured as described above and preincubated for 24 hours with the antisense S-oligonucleotide hTxS-6 at doses ranging from 0.25–40 µM. Following the preincubation period, the cells were stimulated with 10 ng/ml interleukin-1β for 24 hours at which time the media were collected and thromboxane production was measured by measuring the stable metabolite, $TxB_2$, by specific radioimmunoassay.

Figure 11:
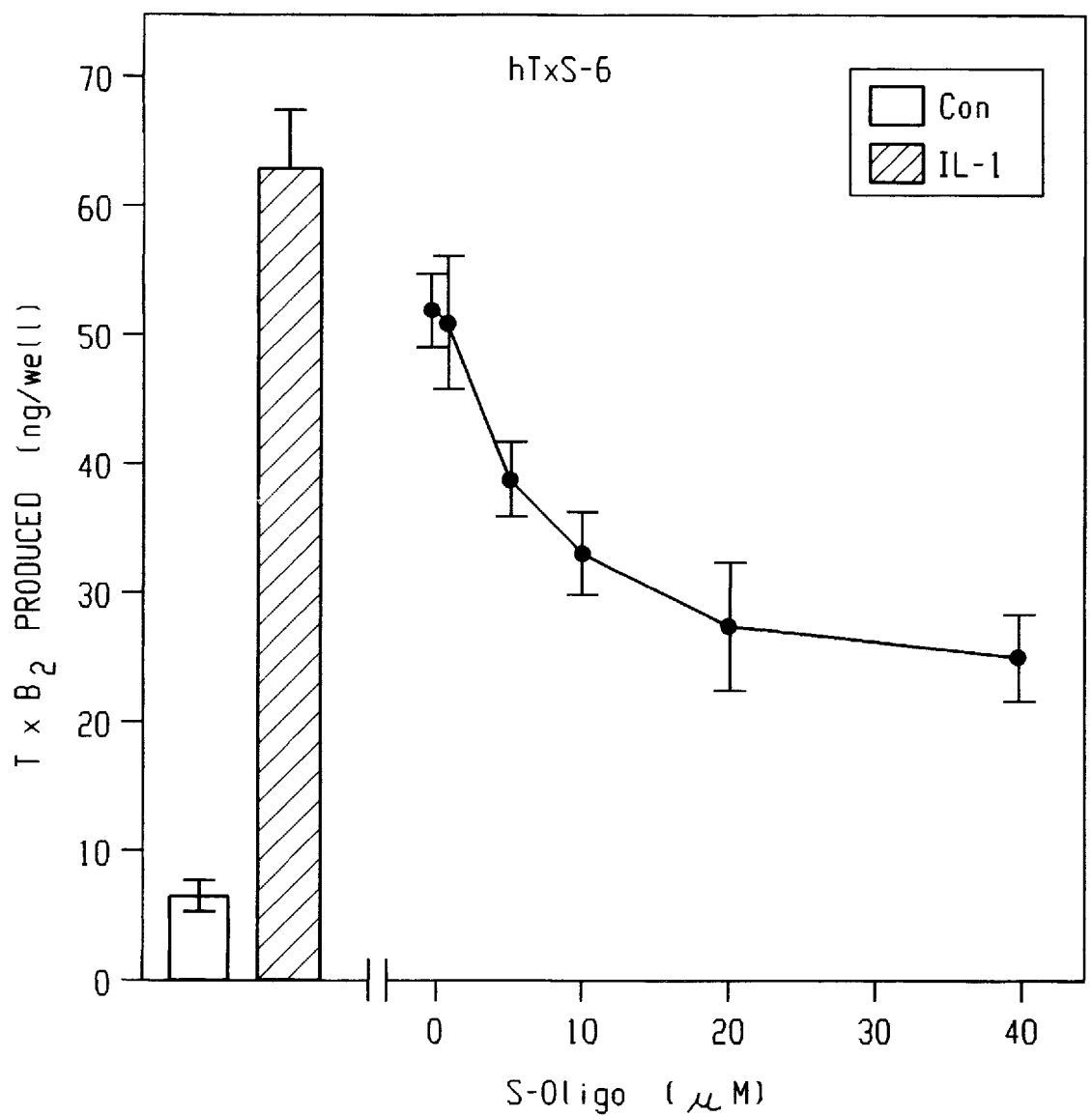
FIG. 11. is a graph demonstrating hTXS antisense S-oligonucleotide suppression of thromboxane production in human $ED_{27}$ cells.

As shown in FIG. 11, S-oligonucleotide hTXS-6 significantly inhibited the production of the TXA synthase. Furthermore there was a dose-dependent inhibitory effect of the antisense S-oligonucleotide directed against human $TxA_2$ synthase.

The antisense nucleotides of the present invention are effective at suppressing cyclooxygenase products such as prostaglandins and thromboxane and are useful in the study and treatment of preterm labor, preeclampsia, PROM, premature cervical effacement and dilation, and endometriosis and menstrual cramping, known as dysmenorrhea.

The antisense oligonucleotides are also suitable for treating disease controlled by prostaglandins such as rheumatoid arthritis, adult respiratory syndrome, and glomerulonephritis.

I claim:

1. An antisense oligonucleotide which inhibits expression of mRNA encoding human cyclooxygenase 2, which antisense oligonucleotide forms a stable hybrid with: a target sequence in the 5' untranslated region and comprising the ATG start codon or a sequence upstream of the ATG start codon of said mRNA; or to a target sequence entirely within the 3' untranslated region of said mRNA.

2. A phosphorothioate derivative of an antisense oligonucleotide which binds to mRNA encoding cyclooxygenase and inhibits the production of cyclooxygenase, wherein the antisense oligonucleotide has a sequence selected from the following group of deoxynucleotide sequences:

5'-GGGAGTGGATGGATGTGC-3', SEQ. ID. No. 25;
5'-AAAACTCCTCCCTCCAGA-3', SEQ. ID. No. 1;
5'-CCACGAAAACCCACATCA-3', SEQ. ID. No. 2;
5'-CCGAAAGTGGCAAAATCA-3', SEQ. ID. No. 3;
5'-TCTGGGAGTGGATGGATG-3', SEQ. ID. No. 4;
5'-AGAGGTGGCAGCGGAGGT-3', SEQ. ID. No. 5;
5'-AGAGGAATCAATGCTGAT-3', SEQ. ID. No. 6;
5'-GAGCATCGCAGAGGTGGC-3', SEQ. ID. No. 7;
5'-TTGGACCCCTTTGTTTGA-3', SEQ. ID. No. 8;
5'-GACTCCGGCTCATGGCGC-3', SEQ. ID. No. 9;
5'-GTAGGCTTTGCTGTCTGA-3', SEQ. ID. No. 10;
5'-CGGGCGAGCATC-3', SEQ. ID. No. 11;
5'-GCAGCGGCGGGCAGGGCG-3', SEQ. ID. No. 12;
5'-GAGCATCGCAGCGGC-3', SEQ. ID. No. 13;
5'-GGCGAGCATCGCAGCGGC-3', SEQ. ID. No 14;
5'-GCGCGGGCGAGCATC-3', SEQ. ID. No. 15;
5'-AGGGCGCGGGCGAGCATC-3', SEQ. ID. No. 16;
5'-ATGACTCCTTTCTCCGCA-3', SEQ. ID. No. 17;
and 5'-TTTTGGCGGGGTTATGGGGT-3', SEQ. ID. No 18.

3. The antisense oligonucleotides of claim 2 wherein the oligonucleotide has the following deoxynucleotide sequence: 5'-AGAGGTGGCAGCGGAGGT-3', SEQ. ID. No. 5.

4. The antisense oligonucleotides of claim 2 wherein the oligonucleotide has the following deoxynucleotide sequence: 5'-AGAGGAATCAATGCTGAT-3', SEQ. ID. No. 6.

5. The antisense oligonucleotides of claim 2 wherein the oligonucleotide has the following deoxynucleotide sequence: 5'-GAGCATCGCAGAGGTGGC-3', SEQ. ID. No. 7.

6. The antisense oligonucleotides of claim 2 wherein the oligonucleotide has the following deoxynucleotide sequence: 5'-TTGGACCCCTTTGTTTGA-3', SEQ. ID. No. 8.

7. The antisense oligonucleotides of claim 2 wherein the oligonucleotide has the following deoxynucleotide sequence: 5'-GACTCCGGCTCATGGCGC-3', SEQ. ID. No. 9.

8. The antisense oligonucleotides of claim 2 wherein the oligonucleotide has the following deoxynucleotide sequence: 5'-GTAGGCTTTGCTGTCTGA-3', SEQ. ID. No. 10.

9. The antisense oligonucleotides of claim 2 wherein the oligonucleotide has the following deoxynucleotide sequence: 5'-CGGGCGAGCATC-3', SEQ. ID. No. 11.

10. The antisense oligonucleotides of claim 2 wherein the oligonucleotide has the following deoxynucleotide sequence: 5'-GCAGCGGCGGGCAGGGCG-3', SEQ. ID. No. 12.

11. The antisense oligonucleotides of claim 2 wherein the oligonucleotide has the following deoxynucleotide sequence: 5'-GAGCATCGCAGCGGC-3', SEQ. ID. No. 13.

12. The antisense oligonucleotides of claim 2 wherein the oligonucleotide has the following deoxynucleotide sequence: 5'-GGCGAGCATCGCAGCGGC-3', SEQ. ID. No. 14.

13. The antisense oligonucleotides of claim 2 wherein the oligonucleotide has the following deoxynucleotide sequence: 5'-GCGCGGGCGAGCATC-3', SEQ. ID. No. 15.

14. The antisense oligonucleotides of claim 2 wherein the oligonucleotide has the following deoxynucleotide sequence: 5'-ATGACTCCTTTCTCCGCA-3', SEQ. ID. No. 17.

15. The antisense oligonucleotides of claim 2 wherein the oligonucleotide has the following deoxynucleotide sequence: 5'-TTTTGGCGGGGTTATGGGGT-3', SEQ. ID. No. 18.

16. An antisense oligonucleotide which inhibits expression of mRNA encoding mouse cyclooxygenase 2, which oligonucleotide forms a stable hybrid with: a target sequence in the 5' untranslated region and comprising the ATG start codon or a sequence upstream of the ATG start codon of said mRNA; or to a target sequence entirely within the 3' untranslated region of said mRNA.

17. An antisense oligonucleotide which inhibits expression of mRNA encoding human cyclooxygenase 1, which oligonucleotide forms a stable hybrid with a target sequence in the 5' untranslated region of said mRNA and comprising the ATG start codon or a sequence upstream of the ATG start codon of said mRNA.

18. The antisense oligonucleotide of claim 1, wherein the oligonucleotide is a phosphorothioate derivative of the antisense oligonucleotide.

19. The antisense oligonucleotide of claim 1, wherein the oligonucleotide has a length of 12 to 20 nucleotides.

20. The antisense oligonucleotide of claim 1 wherein the oligonucleotide is a phosphorothioate derivative of the antisense oligonucleotide and has a length of 12 to 20 nucleotides.

21. The antisense oligonucleotide of claim 16 wherein the oligonucleotide is a phosphorothioate derivative of the antisense oligonucleotide.

22. The antisense oligonucleotide of claim 16 wherein the antisense oligonucleotide has a length of 12 to 20 nucleotides.

23. The antisense oligonucleotide of claim 1 wherein the oligonucleotide forms a stable hybrid with a target sequence in the 5' untranslated region and comprising a sequence upstream of the ATG start codon of said mRNA.

24. The antisense oligonucleotide of claim 1 wherein the oligonucleotide forms a stable hybrid with a target sequence entirely within the 3' untranslated region of said mRNA.

25. The antisense oligonucleotide of claim 1 wherein the oligonucleotide forms a stable hybrid with a target sequence in the 5' untranslated region of said mRNA and comprising the ATG start codon.

26. The antisense oligonucleotide of claim 16 wherein the oligonucleotide forms a stable hybrid with a target sequence in the 5' untranslated region and comprising a sequence upstream of the ATG start codon of said mRNA.

27. The antisense oligonucleotide of claim 16 wherein the oligonucleotide forms a stable hybrid with a target sequence entirely within the 3' untranslated region of said mRNA.

28. The antisense oligonucleotide of claim 16 wherein the oligonucleotide forms a stable hybrid with a target sequence in the 5' untranslated region and comprising the ATG start codon of said mRNA.

29. The antisense oligonucleotide of claim 16 wherein the antisense oligonucleotide is a phosphorothioate derivative of the antisense oligonucleotide and has a length of 12 to 20 nucleotides.

30. The antisense oligonucleotide of claim 17 wherein the antisense oligonucleotide is a phosphorothioate derivative of the antisense oligonucleotide.

31. The antisense oligonucleotide of claim 17 wherein the antisense oligonucleotide has a length of 12 to 20 nucleotides.

32. The antisense oligonucleotide of claim 17 wherein the antisense oligonucleotide is a phosphorothioate derivative of the antisense oligonucleotide and has a length of 12 to 20 nucleotide.

* * * * *

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA to mRNA ( i i i ) HYPOTHETICAL: NO ( i v ) ANTI-SENSE: YES ( x i ) SEQUENCE DESCRIPTION: SEQ ID NO:1:

AAAACTCCTC CCTCCAGA                                                            18

( 2 ) INFORMATION FOR SEQ ID NO:2:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA to mRNA ( i v ) ANTI-SENSE: YES ( x i ) SEQUENCE DESCRIPTION: SEQ ID NO:2:

CCACGAAAAC CCACATCA                                                            18

( 2 ) INFORMATION FOR SEQ ID NO:3:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA to mRNA ( i v ) ANTI-SENSE: YES ( x i ) SEQUENCE DESCRIPTION: SEQ ID NO:3:

CCGAAAGTGG CAAAATCA                                                            18

( 2 ) INFORMATION FOR SEQ ID NO:4:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA to mRNA ( i v ) ANTI-SENSE: YES ( x i ) SEQUENCE DESCRIPTION: SEQ ID NO:4:

TCTGGGAGTG GATGGATG                                                            18

( 2 ) INFORMATION FOR SEQ ID NO:5:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: cDNA to mRNA ( i v ) ANTI-SENSE: YES ( x i ) SEQUENCE DESCRIPTION: SEQ ID NO:5:

AGAGGTGGCA GCGGAGGT                                                                 18

( 2 ) INFORMATION FOR SEQ ID NO:6:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA to mRNA ( i v ) ANTI-SENSE: YES ( x i ) SEQUENCE DESCRIPTION: SEQ ID NO:6:

AGAGGAATCA ATGCTGAT                                                                 18

( 2 ) INFORMATION FOR SEQ ID NO:7:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA to mRNA ( i v ) ANTI-SENSE: YES ( x i ) SEQUENCE DESCRIPTION: SEQ ID NO:7:

GAGCATCGCA GAGGTGGC                                                                 18

( 2 ) INFORMATION FOR SEQ ID NO:8:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA to mRNA ( i v ) ANTI-SENSE: YES ( x i ) SEQUENCE DESCRIPTION: SEQ ID NO:8:

TTGGACCCCT TTGTTTGA                                                                 18

( 2 ) INFORMATION FOR SEQ ID NO:9:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA to mRNA ( i v ) ANTI-SENSE: YES ( x i ) SEQUENCE DESCRIPTION: SEQ ID NO:9:

GACTCCGGCT CATGGCGC                                                                      18

( 2 ) INFORMATION FOR SEQ ID NO:10:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to mRNA ( i v ) ANTI-SENSE: YES ( x i ) SEQUENCE DESCRIPTION: SEQ ID NO:10:

GTAGGCTTTG CTGTCTGA                                                                      18

( 2 ) INFORMATION FOR SEQ ID NO:11:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: cDNA to mRNA ( i v ) ANTI-SENSE: YES ( x i ) SEQUENCE DESCRIPTION: SEQ ID NO:11:

CGGGCGAGCA TC                                                                            12

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to mRNA ( i v ) ANTI-SENSE: YES ( x i ) SEQUENCE DESCRIPTION: SEQ ID NO:12:

GCAGCGGCGG GCAGGGCG                                                                      18

( 2 ) INFORMATION FOR SEQ ID NO:13:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA to mRNA ( i v ) ANTI-SENSE: YES ( x i ) SEQUENCE DESCRIPTION: SEQ ID NO:13:

GAGCATCGCA GCGGC                                                                         15

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to mRNA ( i v ) ANTI-SENSE: YES ( x i ) SEQUENCE DESCRIPTION: SEQ ID NO:14:

GGCGAGCATC GCAGCGGC  18

( 2 ) INFORMATION FOR SEQ ID NO:15:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA to mRNA ( i v ) ANTI-SENSE: YES ( x i ) SEQUENCE DESCRIPTION: SEQ ID NO:15:

GCGCGGGCGA GCATC  15

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to mRNA ( i v ) ANTI-SENSE: YES ( x i ) SEQUENCE DESCRIPTION: SEQ ID NO:16:

AGGGCGCGGG CGAGCATC  18

( 2 ) INFORMATION FOR SEQ ID NO:17:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to mRNA ( i v ) ANTI-SENSE: YES ( x i ) SEQUENCE DESCRIPTION: SEQ ID NO:17:

ATGACTCCTT TCTCCGCA  18

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to mRNA ( i v ) ANTI-SENSE: YES ( x i ) SEQUENCE DESCRIPTION: SEQ ID NO:18:

TTTTGGCGGG GTTATGGGGT  20

( 2 ) INFORMATION FOR SEQ ID NO:19:

( i ) SEQUENCE CHARACTERISTICS:
        ( A ) LENGTH: 18 base pairs (B) TYPE: nucleic acid
                (C) STRANDEDNESS: single
                (D) TOPOLOGY: linear (ii) MOLECULE TYPE: cDNA to mRNA (iv) ANTI-SENSE: YES (xi) SEQUENCE DESCRIPTION: SEQ ID NO:19:

AACCAAGCAA ACATCACA                                                                                        18

(2) INFORMATION FOR SEQ ID NO:20:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (ii) MOLECULE TYPE: cDNA to mRNA (iv) ANTI-SENSE: YES (xi) SEQUENCE DESCRIPTION: SEQ ID NO:20:

TTATGGGAAC CGTGCTCT                                                                                        18

(2) INFORMATION FOR SEQ ID NO:21:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (ii) MOLECULE TYPE: cDNA to mRNA (iv) ANTI-SENSE: YES (xi) SEQUENCE DESCRIPTION: SEQ ID NO:21:

GCTTCCATCA TTCCTCTG                                                                                        18

(2) INFORMATION FOR SEQ ID NO:22:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (ii) MOLECULE TYPE: cDNA to mRNA (iv) ANTI-SENSE: YES (xi) SEQUENCE DESCRIPTION: SEQ ID NO:22:

TAGGGCAGAT TTGGATTC                                                                                        18

(2) INFORMATION FOR SEQ ID NO:23:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (ii) MOLECULE TYPE: cDNA to mRNA (iv) ANTI-SENSE: YES (xi) SEQUENCE DESCRIPTION: SEQ ID NO:23:

GGCTTTCAAT CACTTCAG                                                                                        18

( 2 ) INFORMATION FOR SEQ ID NO:24:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to mRNA ( i v ) ANTI-SENSE: YES ( x i ) SEQUENCE DESCRIPTION: SEQ ID NO:24:

| GGCTTCCATC ATTTCTCT | 18 |
|---|---|

( 2 ) INFORMATION FOR SEQ ID NO:25:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: YES ( x i ) SEQUENCE DESCRIPTION: SEQ ID NO:25:

| GGGAGTGGAT GGATGTGC | 18 |
|---|---|

( 2 ) INFORMATION FOR SEQ ID NO:26:

( i ) SEQUENCE CHARACTERISTICS:
        ( A ) LENGTH: 2757 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:26:

| GCCGTTGGCA | TTGCACATCC | ATCCACTCCC | AGAGTCATGA | GTCGAAGGAG | TCTCTCGCTC | 60 |
|---|---|---|---|---|---|---|
| TGGTTTCCCC | TGCTGCTGCT | CCTGCTGCTG | CCGCCGACAC | CCTCGGTCCT | GCTCGCAGAT | 120 |
| CCTGGGGTGC | CCTCACCAGT | CAATCCCTGT | TGTTACTATC | CGTGCCAGAA | CCAGGGTGTC | 180 |
| TGTGTCCGCT | TTGGCCTCGA | CAACTACCAG | TGTGATTGTA | CTCGCACGGG | CTACTCAGGC | 240 |
| CCCAACTGTA | CCATCCCTGA | GATCTGGACC | TGGCTTCGGA | ATTCTCTGCG | GCCCAGCCCC | 300 |
| TCGTTCACCC | ATTTCCTGCT | GACACATGGA | TACTGGCTCT | GGGAATTTGT | GAATGCCACC | 360 |
| TTCATCCGAG | AAGTACTCAT | GCGCCTGGTA | CTCACAGTGC | GGTCCAACCT | TATCCCCAGC | 420 |
| CCTCCGACCT | ACAACTCAGC | GCATGACTAC | ATCAGCTGGG | AGTCCTTCTC | CAATGTGAGC | 480 |
| TACTATACTC | GCATTCTGCC | CTCTGTACCC | AAAGACTGCC | CCACACCCAT | GGGGACCAAA | 540 |
| GGGAAGAAAC | AGTTACCAGA | TGTTCAGCTT | CTGGCCCAAC | AGCTGCTGCT | GAGAAGGGAG | 600 |
| TTCATTCCTG | CCCCCCAGGG | CACCAACATC | CTGTTTGCCT | TCTTTGCACA | ACACTTCACC | 660 |
| CACCAGTTCT | TCAAGACCTC | TGGAAAGATG | GGTCCTGGCT | TACCAAGGC | CTTAGGCCAC | 720 |
| GGGGTAGACC | TTGGCCACAT | TTATGGAGAT | AATCTGGAAC | GACAGTATCA | CCTGCGGCTC | 780 |
| TTCAAGGATG | GGAAACTTAG | GTACCAGGTG | CTGGACGGAG | AGGTGTACCC | ACCTTCCGTG | 840 |

```
GAACAGGCGT   CCGTGTTGAT   GCGCTACCCA   CCAGGTGTCC   CGCCTGAAAG   GCAGATGGCT    900

GTGGGCCAGG   AGGTGTTTGG   GTTGCTTCCG   GGGCTGATGC   TCTTCTCCAC   GATCTGGCTT    960

CGTGAACATA   ACCGCGTGTG   CGACCTGCTG   AAGGAGGAGC   ATCCACGTG    GGATGATGAG    1020

CAGCTCTTCC   AGACCACTCG   CCTCATCCTT   ATAGGAGAAA   CCATCAAAAT   TGTCATTGAG    1080

GAGTATGTGC   AGCACTTGAG   TGGCTATTTC   CTGCAGCTCA   AGTTTGACCC   GGAGCTGCTG    1140

TTCCGAGCCC   AGTTCCAATA   TCGAAACCGC   ATCGCCATGG   AATTTAACCA   TCTCTATCAC    1200

TGGCATCCAC   TCATGCCCAA   CTCCTTCCAA   GTGGGCTCAC   AAGAGTACAG   CTACGAGCAG    1260

TTTTTATTTA   ACACTTCTAT   GCTGGTGGAC   TATGGGGTTG   AGGCACTGGT   GGATGCCTTC    1320

TCTCGCCAGA   GGGCTGGCCG   GATTGGTGGA   GGTAGGAACT   TTGACTATCA   TGTTCTGCAT    1380

GTGGCTGTGG   ATGTCATCAA   GGAGTCCCGA   GAGATGCGCC   TACAGCCCTT   CAATGAATAC    1440

CGAAAGAGGT   TTGGCTTGAA   GCCTTACACC   TCTTTCCAGG   AGCTCACAGG   AGAGAAGGAG    1500

ATGGCTGCTG   AGTTGGAGGA   GCTGTACGGT   GACATCGATG   CTTTAGAGTT   CTACCCGGGG    1560

TTGCTGCTGG   AGAAGTGCCA   GCCCAACTCC   ATCTTTGGAG   AAAGTATGAT   AGAGATGGGG    1620

GCTCCCTTTT   CCCTCAAGGG   CCTCCTAGGG   AATCCCATCT   GTTCCCAGA    GTACTGGAAA    1680

CCCAGCACGT   TCGGTGGTGA   CGTGGGCTTC   AACCTTGTCA   ACACAGCCTC   ACTGAAGAAA    1740

CTGGTCTGCC   TCAACACCAA   GACCTGCCCC   TATGTTTCCT   TCCGTGTGCC   AGATTACCCT    1800

GGAGATGACG   GGTCTGTCTT   AGTGAGACGC   TCCACTGAGC   TCTGAGGGAG   CTGGAAAGCA    1860

GCCTCTGGAG   GGAGGAGTTT   TGTTCCTGAT   GAGGACAAGT   CCTTGATGTG   GGTTTTCGTG    1920

GCTTGGCATT   GTGAGAGCTG   ATGCTCACAT   TTGAAACTTT   GGGTCTTACC   CTTGCCTAGA    1980

AAATTGTGAT   TTTGCCACTT   TCGGATGTTG   AATTCTTTGT   TAACTAAGAA   AGTTAGAAGT    2040

GGTTTTGTCT   GCCTCCTCAG   AACTTGGCTC   TTTGTTGGCA   ACTCAGAAAG   TCAGATTTCT    2100

GGTTGATTTG   GAATATAGGC   TTAAAACTTT   ATATTATAGG   GTAGGGTGTG   GTTGCACACA    2160

CCTTAATCCC   AGCACTTGGA   AGGCAGAGGC   AGTTGGATCT   CTGGGAGTTT   GAGGCCAGTT    2220

TGGCCTATAT   AGTGAGTTCT   AGGCCAGCCA   TGGATGCATA   GTGAGACTCT   TTCTCAAAAC    2280

AAACAAACAA   ACAAACAAAC   AAACAACTTT   TAGAATGTAG   AATTCCGTAA   AAAAAAAAA    2340

TCCCTTGAAA   GTTAATGGGG   TCCTCAATTT   TCTTCCTAGA   ATTTGGAGGC   CTCTTCAGAA    2400

TGTTGACTAT   CTGACAGGTG   ACTCAGAAGG   TCCTGTTCCT   GGTCAATGAT   CTATAACATG    2460

GGCCAAAACA   TTCCCAACTT   GAATGTCTAG   AATGTGGAAT   TGGTTCATTT   TCCTGTTCAG    2520

TGAAATGGAC   ACAGAACAAA   AGAACCCAGT   GTCCAGCAAG   AATTGCCTTG   CCCAAACCTA    2580

CGTCTACGCC   AAAGGTCAAG   GCAGTAAGGT   GTTCTTGGGA   GCCACACTTA   GACTCTTTCC    2640

AAAGATGTGG   AGGGAACAGA   TGGACTCATC   TATGATCTTG   GTTGGAAACC   ACCACAGTTC    2700

TATCCCCATC   CAGATCTTTG   CTTGTGGCAG   CTGTTTCTCA   TGAAGCTAAT   AAAATTC      2757
```

( 2 ) INFORMATION FOR SEQ ID NO:27:

( i ) SEQUENCE CHARACTERISTICS:
        ( A ) LENGTH: 3986 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:27:

```
AGTTGTCAAA  CTGCGAGCTA  AGAGCTTCAG  GAGTCAGTCA  GGACTCTGCT  CACGAAGAAT    60
CTCAGCACTG  CATCCTGCCA  GCTCCACCGC  CACCACCACT  GCCACCTCCG  CTGCCACCTC   120
TGCGATGCTC  TTCCGAGCTG  TGCTGCTCTG  CGCTGCCCTG  GGGCTCAGCC  AGGCAGCAAA   180
TCCTTGCTGT  TCCAATCCAT  GTCAAAACCG  TGGGGAATGT  ATGAGCACAG  GATTTGACCA   240
GTATAAGTGT  GACTGTACCC  GGACTGGATT  CTATGGTGAA  AACTGTACTA  CACCTGAATT   300
TCTGACAAGA  ATCAAATTAC  TGCTGAAGCC  CACCCCAAAC  ACAGTGCACT  ACATCCTGAC   360
CCACTTCAAG  GGAGTCTGGA  ACATTGTGAA  CAACATCCCC  TTCCTGCGAA  GTTTAACTAT   420
GAAATATGTG  CTGACATCCA  GATCATATTT  GATTGACAGT  CCACCTACTT  ACAATGTGCA   480
CTATGGTTAC  AAAAGCTGGG  AAGCCTTCTC  CAACCTCTCC  TACTACACCA  GGGCCCTTCC   540
TCCAGTAGCA  GATGACTGCC  CAACTCCCAT  GGGTGTGAAG  GGAAATAAGG  AGCTTCCTGA   600
TTCAAAAGAA  GTGCTGGAAA  AGGTTCTTCT  ACGGAGAGAG  TTCATCCCTG  ACCCCCAAGG   660
CTCAAATATG  ATGTTTGCAT  TCTTTGCCCA  GCACTTCACC  CATCAGTTTT  TCAAGACAGA   720
TCATAAGCGA  GGACCTGGGT  TCACCCGAGG  ACTGGGCCAT  GGAGTGGACT  TAAATCACAT   780
TTATGGTGAA  ACTCTGGACA  GACAACATAA  ACTGCGCCTT  TTCAAGGATG  GAAAATTGAA   840
ATATCAGGTC  ATTGGTGGAG  AGGTGTATCC  CCCCACAGTC  AAAGACACTC  AGGTAGAGAT   900
GATCTACCCT  CCTCACATCC  CTGAGAACCT  GCAGTTTGCT  GTGGGGCAGG  AAGTCTTTGG   960
TCTGGTGCCT  GGTCTGATGA  TGTATGCCAC  CATCTGGCTT  CGGGAGCACA  ACAGAGTGTG  1020
CGACATACTC  AAGCAGGAGC  ATCCTGAGTG  GGGTGATGAG  CAACTATTCC  AAACCAGCAG  1080
ACTCATACTC  ATAGGAGAGA  CTATCAAGAT  AGTGATCGAA  GACTACGTGC  AACACCTGAG  1140
CGGTTACCAC  TTCAAACTCA  AGTTTGACCC  AGAGCTCCTT  TTCAACCAGC  AGTTCCAGTA  1200
TCAGAACCGC  ATTGCCTCTG  AATTCAACAC  ACTCTATCAC  TGGCACCCCC  TGCTGCCCGA  1260
CACCTTCAAC  ATTGAAGACC  AGGAGTACAG  CTTCAAACAG  TTTCTCTACA  CAACTCCAT   1320
CCTCCTGGAA  CATGGACTCA  CTCAGTTTGT  TGAGTCATTC  ACCAGACAGA  TTGCTGGCCG  1380
GGTTGCTGGG  GGAAGAAATG  TGCCAATTGC  TGTACAAGCA  GTGGCAAAGG  CCTCCATTGA  1440
CCAGAGCAGA  GAGATGAAAT  ACCAGTCTCT  CAATGAGTAC  CGCAAACGCT  TCTCCCTGAA  1500
GCCGTACACA  TCATTTGAAG  AACTTACAGG  AGAGAAGGAA  ATGGCTGCAG  AATTGAAAGC  1560
CCTCTACAGT  GACATCGATG  TCATGGAACT  GTACCCTGCC  CTGCTGGTGG  AAAAACCTCG  1620
TCCAGATGCT  ATCTTTGGGG  AGACCATGGT  AGAGCTTGGA  GCACCATTCT  CCTTGAAAGG  1680
ACTTATGGGA  AATCCCATCT  GTTCTCCTCA  ATACTGGAAG  CCGAGCACCT  TTGGAGGCGA  1740
AGTGGGTTTT  AAGATCATCA  ATACTGCCTC  AATTCAGTCT  CTCATCTGCA  ATAATGTGAA  1800
GGGGTGTCCC  TTCACTTCTT  TCAATGTGCA  AGATCCACAG  CCTACCAAAA  CAGCCACCAT  1860
CAATGCAAGT  GCCTCCCACT  CCAGACTAGA  TGACATTAAC  CCTACAGTAC  TAATCAAAAG  1920
GCGTTCAACT  GAGCTGTAAA  AGTCTACTGA  CCATATTTAT  TTATTTATGT  GAAGGAATTT  1980
AATTTAATTA  TTTAATATTT  ATACTGAATT  TTTTTTCATG  TAACATCTTC  CATAACAGAA  2040
GGCAATGTTC  TTGAACAATG  TTACATTTGT  GAAGATTCCT  CCGGTGTTTG  TCCTTTAAAT  2100
ATGTGTTACC  TGAAACTGAA  AGGAAATCAG  CATTCATTCC  TCTACATAAG  CCAGTGAGAA  2160
GGGAAATGAA  TTTTGATATC  TTTATACTTG  AATTTCAGAT  CATGAATTAG  CTTAACAAGA  2220
ACCAAGGAAA  AATGTATGAA  TATGTGAGTG  TTGTTACAAG  ATGAAAAATG  CTGCAGGTAT  2280
CAACACTGTT  GGTTACACTG  TGTCTTCTTT  ACCTATGATA  GGAGCATGTA  ATGTGGAATT  2340
```

| | | | | | | |
|---|---|---|---|---|---|---|
| CGTCTTAAAT | CCTTGCATAT | CTTTATCTCA | TCAAACAAAG | GGGTCCAAGT | TCAGTTTTAA | 2400 |
| ATAAGCATTT | AAGGCAGATA | CTGACAACAA | TCTCATTTTT | TTAAAATGTT | GTCTTGAGAC | 2460 |
| AAATAATTTG | AAATTCTAA | ATTGGGACGT | TTGAATCACT | TTTGAAAGCT | CTTACTTTCT | 2520 |
| TAAGCTGTCA | GGTTTGTACC | GACATGGAGT | AAACAGCTAT | CATAAACGTA | AATCTCCAAA | 2580 |
| ACTAGTAGAA | ATTATGTCAT | GATTGATGGT | TAAGATACCA | TGTCAGGGAT | TGTCTTTTCT | 2640 |
| TAGAAGTAGT | GAAAGCTACT | TACTATGACA | ATCAGACCTT | CCTTGTATGT | CAAAATGCTG | 2700 |
| GTGTGGAAGG | TGGTGGAGCC | CGTGCTGCTC | TGTCTTAACT | ATGAGTGTGA | GCTTTAAAGC | 2760 |
| TCGTTGATGA | GTGGTAGCCA | GCAAAGCCTA | GAGCAACAAA | AGCGTTCTAC | AAAGGAACTA | 2820 |
| ACCAAGAACA | AAGAAGGGTT | CCCAATTAAA | GATCACATTC | AGGGTTAAAC | TTCCAAAGGA | 2880 |
| GACATCCTGA | TCCTGGTTTT | GTGCTGGCCT | GGTACTCAGT | AGGTTTTGC | TGTGAGGTTA | 2940 |
| AAGACTTGCC | AGGGCTGAAC | TTCGAAACAG | TTTTTCTGTT | GCACAGTATG | ATGTAACAGT | 3000 |
| CCATCTCTCA | ATGCAATAGG | TATCAGTGGC | CTCGTGAGCT | TCTTCACAAT | ATTTGATATG | 3060 |
| TCTTCCAGCC | CATTGAACCT | GGACTGCAGA | AGGCCCATG | TCATGTGTGA | GCTCAGCCTG | 3120 |
| GATGCCAGCA | TTTGCTGCTC | CTCTTAGTTC | CGTTCTCGT | GGTCACTTTA | CTACGAGAAA | 3180 |
| CGCTGATTGG | GTTTTCGTAG | CTGTGTTACC | AGGTTTTAG | TATCAGAACT | ATTCTTTCTT | 3240 |
| TAACCTCTAT | TCATATTTTC | TCTACTTGAA | GTTTACATT | CAGGAAAACC | TCAGCGCTCA | 3300 |
| GGACTACTAT | GTACCTCCCC | TTTGGAGGGA | AAAATTCATT | TTTAGGTAAA | AGGCAAAAAT | 3360 |
| TTTTTAAAAA | TATTTTTTAT | TTATAATTAT | ATGGAAGGGC | CCTACCAAGA | TGCTAGAAAT | 3420 |
| ATAGGGAGTT | CCTGACAAGA | AATTTCCATT | CTTATTCTGA | AGAATTGCTT | TCTTACTTAA | 3480 |
| AAACAAAGAC | AGTTTGTGAG | TAGTTCTGGG | CAATAGGGAT | AAATATAAAA | CAATAATGAT | 3540 |
| GATCATTTTC | TACATCTCAT | TATCAGCTGA | GGTACTGTAT | ATTACTGAAT | TTATTGAAGA | 3600 |
| TAGTTATGTC | TTTTAGACAT | TGTTGTTATA | AACTATGTTT | AAGCCTACTA | CAAGTGTTTC | 3660 |
| TTTTTTGCAT | TATGTTGGAA | TTGATGTACC | TTTTTTATGA | TTACCTCTCT | GAACTATGGT | 3720 |
| GTGAACAATC | AAACAAAATG | ATGAGATTAA | CGTTCATGGA | TAAATTCTAA | GAAAACTAGT | 3780 |
| GTATTTTTTT | GAAAAGTTTG | AAGTTAGAAC | TTAGGCTGTT | GGAATTTACG | CATAAAGCAG | 3840 |
| ACTGCATAGG | ATCCAATATT | GACTGACCCA | AGCATGTTAT | AAAGACTGAC | ATTTTAGACA | 3900 |
| TTTTGAAGGC | CCTGTAAGTG | TTTATTAATT | AGTTAGAACT | TAATTGATTA | AAAAATATAT | 3960 |
| CCAAAGCACT | ATAGGCATTA | GAATTC | | | | 3986 |

( 2 ) INFORMATION FOR SEQ ID NO:28:

( i ) SEQUENCE CHARACTERISTICS:
        ( A ) LENGTH: 2554 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:28:

| | | | | | | |
|---|---|---|---|---|---|---|
| GCGCCATGAG | CCGGAGTCTC | TTGCTCCGGT | TCTTGCTGTT | CCTGCTCCTG | CTCCCGCCGC | 60 |
| TCCCCGTCCT | GCTCGCGGAC | CCAGGGGCGC | CCACGCCAGT | GAATCCCTGT | TGTTACTATC | 120 |
| CATGCCAGCA | CCAGGGCATC | TGTGTCCGCT | TCGGCCTTGA | CCGCTACCAG | TGTGACTGCA | 180 |
| CCCGCACGGC | TATTCCGGCC | CCAACTGCAC | CATCCCTGGC | CTGTGGACCT | GGCTCCGGAA | 240 |

```
ATTCACTGCG  GCCCAGCCCC  TCTTTCACCC  ACTTCCTGCT  CACTCACGGG  CGCTGGTTCT   300
GGGAGTTTGT  CAATGCCACC  TTCATCCGAG  AGATGCTCAT  GCGCCTGGTA  CTCACAGTGC   360
GCTCCAACCT  TATCCCCAGT  CCCCCCACCT  ACAACTCAGC  ACATGACTAC  ATCAGCTGGG   420
AGTCTTTCTC  CAACGTGAGC  TATTACACTC  GTATTCTGCC  CTCTGTGCCT  AAAGATTGCC   480
CCACACCCAT  GGGAACCAAA  GGGAAGAAGC  AGTTGCCAGA  TGCCCAGCTC  CTGGCCCGCC   540
GCTTCCTGCT  CAGGAGGAAG  TTCATACCTG  ACCCCAAGG   CACCAACCTC  ATGTTTGCCT   600
TCTTTGCACA  ACACTTCACC  CACCAGTTCT  TCAAAACTTC  TGGCAAGATG  GGTCCTGGCT   660
TCACCAAGGC  CTTGGGCCAT  GGGGTAGACC  TCGGCCACAT  TTATGGAGAC  AATCTGGAGC   720
GTCAGTATCA  ACTGCGGCTC  TTTAAGGATG  GGAAACTCAA  GTACCAGGTG  CTGGATGGAG   780
AAATGTACCC  GCCCTCGGTA  GAAGAGGCGC  CTGTGTTGAT  GCACTACCCC  CGAGGCATCC   840
CGCCCCAGAG  CCAGATGGCT  GTGGGCCAGG  AGGTGTTTGG  GCTGCTTCCT  GGGCTCATGC   900
TGTATGCCAC  GCTCTGGCTA  CGTGAGCACA  ACCGTGTGTG  TGACCTGCTG  AAGGCTGAGC   960
ACCCCACCTG  GGGCGATGAG  CAGCTTTTCC  AGACGACCCG  CCTCATCCTC  ATAGGGGAGA  1020
CCATCAAGAT  TGTCATCGAG  GAGTACGTGC  AGCAGCTGAG  TGGCTATTTC  CTGCAGCTGA  1080
AATTTGACCC  AGAGCTGCTG  TTCGGTGTCC  AGTTCCAATA  CCGCAACCGC  ATTGCCATGG  1140
AGTTCAACCA  TCTCTACCAC  TGGCACCCCC  TCATGCCTGA  CTCCTTCAAG  GTGGGCTCCC  1200
AGGAGTACAG  CTACGAGCAG  TTCTTGTTCA  ACACCTCCAT  GTTGGTGGAC  TATGGGGTTG  1260
AGGCCCTGGT  GGATGCCTTC  TCTCGCCAGA  TTGCTGGCCG  GATCGGTGGG  GGCAGGAACA  1320
TGGACCACCA  CATCCTGCAT  GTGGCTGTGG  ATGTCATCAG  GGAGTCTCGG  GAGATGCGGC  1380
TGCAGCCCTT  CAATGAGTAC  CGCAAGAGGT  TTGGCATGAA  ACCCTACACC  TCCTTCCAGG  1440
AGCTCGTAGG  AGAGAAGGAG  ATGGCAGCAG  AGTTGGAGGA  ATTGTATGGA  GACATTGATG  1500
CGTTGGAGTT  CTACCCTGGA  CTGCTTCTTG  AAAAGTGCCA  TCCAAACTCT  ATCTTTGGGG  1560
AGAGTATGAT  AGAGATTGGG  GCTCCCTTTT  CCCTCAAGGG  TCTCCTAGGG  AATCCCATCT  1620
GTTCTCCGGA  GTACTGGAAG  CCGAGCACAT  TTGGCGGCGA  GGTGGGCTTT  AACATTGTCA  1680
AGACGGCCAC  ACTGAAGAAG  CTGGTCTGCC  TCAACACCAA  GACCTGTCCC  TACGTTTCCT  1740
TCCGTGTGCC  GGATGCCAGT  CAGGATGATG  GGCCTGCTGT  GGAGCGACCA  TCCACAGAGC  1800
TCTGAGGGGC  AGGAAAGCAG  CATTCTGGAG  GGGAGAGCTT  TGTGCTTGTC  ATTCCAGAGT  1860
GCTGAGGCCA  GGGCTGATGG  TCTTAAATGC  TCATTTTCTG  GTTTGGCATG  GTGAGTGTTG  1920
GGGTTGACAT  TTAGAACTTT  AAGTCTCACC  CATTATCTGG  AATATTGTGA  TTCTGTTTAT  1980
TCTTCCAGAA  TGCTGAACTC  CTTGTTAGCC  CTTCAGATTG  TTAGGAGTGG  TTCTCATTTG  2040
GTCTGCCAGA  ATACTGGGTT  CTTAGTTGAC  AACCTAGAAT  GTCAGATTTC  TGGTTGATTT  2100
GTAACACAGT  CATTCTAGGA  TGTGGAGCTA  CTGATGAAAT  CTGCTAGAAA  GTTAGGGGT   2160
TCTTATTTTG  CATTCCAGAA  TCTTGACTTT  CTGATTGGTG  ATTCAAAGTG  TTGTGTTCCC  2220
TGGCTGATGA  TCCAGAACAG  TGGCTCGTAT  CCCAAATCTG  TCAGCATCTG  GCTGTCTAGA  2280
ATGTGGATTT  GATTCATTTT  CCTGTTCAGT  GAGATATCAT  AGAGACGGAG  ATCCTAAGGT  2340
CCAACAAGAA  TGCATTCCCT  GAATCTGTGC  CTGCACTGAG  AGGGCAAGGA  AGTGGGTGT   2400
TCTTCTTGGG  ACCCCCACTA  AGACCCTGGT  CTGAGGATGT  AGAGAGAACA  GGTGGGCTGT  2460
ATTCACGCCA  TTGGTTGGAA  GCTACCAGAG  CTCTATCCCC  ATCCAGGTCT  TGACTCATGG  2520
CAGCTGTTTC  TCATGAAGCT  AATAAAATTC  GCCC                                2554
```

( 2 ) INFORMATION FOR SEQ ID NO:29:

( i ) SEQUENCE CHARACTERISTICS:
        ( A ) LENGTH: 3387 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:29:

```
GTCCAGGAAC TCCTCAGCAG CGCCTCCTTC AGCTCCACAG CCAGACGCCC TCAGACAGCA      60
AAGCCTACCC CCGCGCCGCG CCCTGCCCGC CGCTGCGATG CTCGCCCGCG CCCTGCTGCT     120
GTGCGCGGTC CTGGCGCTCA GCCATACAGC AAATCCTTGC TGTTCCCACC CATGTCAAAA     180
CCGAGGTGTA TGTATGAGTG TGGGATTTGA CCAGTATAAG TGCGATTGTA CCCGGACAGG     240
ATTCTATGGA GAAAACTGCT CAACACCGGA ATTTTGACA AGAATAAAAT TATTTCTGAA      300
ACCCACTCCA AACACAGTGC ACTACATACT TACCCACTTC AAGGGATTTT GGAACGTTGT     360
GAATAACATT CCCTTCCTTC GAAATGCAAT TATGAGTTAT GTGTTGACAT CCAGATCACA     420
TTTGATTGAC AGTCCACCAA CTTACAATGC TGACTATGGC TACAAAAGCT GGGAAGCCTT     480
CTCTAACCTC TCCTATTATA CTAGAGCCCT TCCTCCTGTG CCTGATGATT GCCCGACTCC     540
CTTGGGTGTC AAAGGTAAAA AGCAGCTTCC TGATTCAAAT GAGATTGTGG AAAATTGCT      600
TCTAAGAAGA AAGTTCATCC CTGATCCCCA GGGCTCAAAC ATGATGTTTG CATTCTTTGC     660
CCAGCACTTC ACGCATCAGT TTTTCAAGAC AGATCATAAG CGAGGGCCAG CTTTCACCAA     720
CGGGCTGGGC CATGGGGTGG ACTTAAATCA TATTTACGGT GAAACTCTGG CTAGACAGCG     780
TAAACTGCGC CTTTTCAAGG ATGGAAAAAT GAAATATCAG ATAATTGATG GAGAGATGTA     840
TCCTCCCACA GTCAAAGATA CTCAGGCAGA GATGATCTAC CCTCCTCAAG TCCCTGAGCA     900
TCTACGGTTT GCTGTGGGGC AGGAGGTCTT TGGTCTGGTG CCTGGTCTGA TGATGTATGC     960
CACAATCTGG CTGAGGGAAC ACAACAGAGT ATGCGATGTG CTTAAACAGG AGCATCCTGA    1020
ATGGGGTGAT GAGCAGTTGT TCCAGACAAG CAGGCTAATA CTGATAGGAG AGACTATTAA    1080
GATTGTGATT GAAGATTATG TGCAACACTT GAGTGGCTAT CACTTCAAAC TGAAATTTGA    1140
CCCAGAACTA CTTTTCAACA AACAATTCCA GTACCAAAAT CGTATTGCTG CTGAATTTAA    1200
CACCCTCTAT CACTGGCATC CCCTTCTGCC TGACACCTTT CAAATTCATG ACCAGAAATA    1260
CAACTATCAA CAGTTTATCT ACAACAACTC TATATTGCTG GAACATGGAA TTACCCAGTT    1320
TGTTGAATCA TTCACCAGGC AAATTGCTGG CAGGGTTGCT GGTGGTAGGA ATGTTCCACC    1380
CGCAGTACAG AAAGTATCAC AGGCTTCCAT TGACCAGAGC AGGCAGATGA AATACCAGTC    1440
TTTTAATGAG TACCGCAAAC GCTTTATGCT GAAGCCCTAT GAATCATTTG AAGAACTTAC    1500
AGGAGAAAAG GAAATGTCTG CAGAGTTGGA AGCACTCTAT GGTGACATCG ATGCTGTGGA    1560
GCTGTATCCT GCCCTTCTGG TAGAAAAGCC TCGGCCAGAT GCCATCTTTG GTGAAACCAT    1620
GGTAGAAGTT GGAGCACCAT TCTCCTTGAA AGGACTTATG GGTAATGTTA TATGTTCTCC    1680
TGCCTACTGG AAGCCAAGCA CTTTTGGTGG AGAAGTGGGT TTTCAAATCA TCAACACTGC    1740
CTCAATTCAG TCTCTCATCT GCAATAACGT GAAGGGCTGT CCCTTTACTT CATTCAGTGT    1800
TCCAGATCCA GAGCTCATTA AAACAGTCAC CATCAATGCA AGTTCTTCCC GCTCCGGACT    1860
AGATGATATC AATCCCACAG TACTACTAAA AGAACGTTCG ACTGAACTGT AGAAGTCTAA    1920
```

-continued

| | | | | | | |
|---|---|---|---|---|---|---|
| TGATCATATT | TATTTATTTA | TATGAACCAT | GTCTATTAAT | TTAATTATTT | AATAATATTT | 1980 |
| ATATTAAACT | CCTTATGTTA | CTTAACATCT | TCTGTAACAG | AAGTCAGTAC | TCCTGTTGCG | 2040 |
| GAGAAAGGAG | TCATACTTGT | GAAGACTTTT | ATGTCACTAC | TCTAAAGATT | TTGCTGTTGC | 2100 |
| TGTTAAGTTT | GGAAAACAGT | TTTTATTCTG | TTTTATAAAC | CAGAGAGAAA | TGAGTTTTGA | 2160 |
| CGTCTTTTTA | CTTGAATTTC | AACTTATATT | ATAAGGACGA | AAGTAAAGAT | GTTTGAATAC | 2220 |
| TTAAACACTA | TCACAAGATG | CCAAAATGCT | GAAAGTTTTT | ACACTGTCGA | TGTTTCCAAT | 2280 |
| GCATCTTCAA | TGATGCATTA | GAAGTAACTA | ATGTTTGAAA | TTTTAAAGTA | CTTTTGGGTA | 2340 |
| TTTTTCTGTC | ATCAAACAAA | ACAGGTATCA | GTGCATTATT | AAATGAATAT | TTAAATTAGA | 2400 |
| CATTACCAGT | AATTTCATGT | CTACTTTTTA | AAATCAGCAA | TGAAACAATA | ATTTGAAATT | 2460 |
| TCTAAATTCA | TAGGGTAGAA | TCACCTGTAA | AAGCTTGTTT | GATTTCTTAA | AGTTATTAAA | 2520 |
| CTTGTACATA | TACCAAAAAG | AAGCTGTCTT | GGATTTAAAT | CTGTAAAATC | AGATGAAATT | 2580 |
| TTACTACAAT | TGCTTGTTAA | AATATTTTAT | AAGTGATGTT | CCTTTTCCAC | CAAGAGTATA | 2640 |
| AACCTTTTTA | GTGTGACTGT | TAAAACTTCC | TTTTAAATCA | AAATGCCAAA | TTTATTAAGG | 2700 |
| TGGTGGAGCC | ACTGCAGTGT | TATCTCAAAA | TAAGAATATC | CTGTTGAGAT | ATTCCAGAAT | 2760 |
| CTGTTTATAT | GGCTGGTAAC | ATGTAAAAAC | CCCATAACCC | CGCCAAAAGG | GGTCCTACCC | 2820 |
| TTGAACATAA | AGCAATAACC | AAAGGAGAAA | AGCCCAAATT | ATTGGTTCCA | AATTTAGGGT | 2880 |
| TTAAACTTTT | TGAAGCAAAC | TTTTTTTTAG | CCTTGTGCAC | TGCAGACCTG | GTACTCAGAT | 2940 |
| TTTGCTATGA | GGTTAATGAA | GTACCAAGCT | GTGCTTGAAT | AACGATATGT | TTTCTCAGAT | 3000 |
| TTTCTGTTGT | ACAGTTTAAT | TTAGCAGTCC | ATATCACATT | GCAAAGTAG | CAATGACCTC | 3060 |
| ATAAAATACC | TCTTCAAAAT | GCTTAAATTC | ATTTCACACA | TTAATTTTAT | CTCAGTCTTG | 3120 |
| AAGCCAATTC | AGTAGGTGCA | TTGGAATCAA | GCCTGGCTAC | CTGCATGCTG | TTCCTTTTCT | 3180 |
| TTTCTTCTTT | TAGCCATTTT | GCTAAGAGAC | ACAGTCTTCT | CAAACACTTC | GTTTCTCCTA | 3240 |
| TTTTGTTTTA | CTAGTTTTAA | GATCAGAGTT | CACTTTCTTT | GGACTCTGCC | TATATTTTCT | 3300 |
| TACCTGAACT | TTTGCAAGTT | TTCAGGTAAA | CCTCAGCTCA | GGACTGCTAT | TTAGCTCCTC | 3360 |
| TTAAGAAGAT | TAAAAAAAAA | AAAAAAG | | | | 3387 |